(12) United States Patent
Noda et al.

(10) Patent No.: US 8,211,075 B2
(45) Date of Patent: Jul. 3, 2012

(54) INTERLABIAL PAD

(75) Inventors: Yuki Noda, Mitoyo-gun (JP); Satoshi Mizutani, Mitoyo-gun (JP); Wataru Yoshimasa, Mitoyo-gun (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 735 days.

(21) Appl. No.: 11/202,579

(22) Filed: Aug. 11, 2005

(65) Prior Publication Data

US 2006/0036228 A1  Feb. 16, 2006

(30) Foreign Application Priority Data

Aug. 12, 2004  (JP) .................................. 2004-235591

(51) Int. Cl.
*A61F 13/15* (2006.01)
*A61F 13/20* (2006.01)
(52) U.S. Cl. ............... 604/385.17; 604/385.01; 604/367
(58) Field of Classification Search .................. 604/378, 604/366, 385, 385.01, 385.17
See application file for complete search history.

(56) References Cited

U.S. PATENT DOCUMENTS

| | | | | |
|---|---|---|---|---|
| 4,595,392 A | * | 6/1986 | Johnson et al. | 604/385.17 |
| 4,673,403 A | * | 6/1987 | Lassen et al. | 604/385.17 |
| 5,672,165 A | * | 9/1997 | Belecky et al. | 604/383 |
| 6,254,584 B1 | * | 7/2001 | Osborn et al. | 604/385.17 |
| 6,617,490 B1 | * | 9/2003 | Chen et al. | 604/380 |
| 6,811,549 B2 | * | 11/2004 | Fleming | 604/385.17 |
| 2004/0216569 A1 | * | 11/2004 | Mizutani et al. | 83/13 |

FOREIGN PATENT DOCUMENTS

| | | |
|---|---|---|
| JP | 2001-507597 A | 6/2001 |
| JP | 2004-097693 A | 4/2004 |
| JP | 2005-503193 A | 2/2005 |
| TW | 368408 | 9/1999 |
| TW | 454503 | 9/2001 |
| WO | WO-98/29075 | 7/1998 |
| WO | WO-02/100315 | 12/2002 |

OTHER PUBLICATIONS

Taiwanese Office Action mailed May 6, 2011, directed to corresponding Taiwanese Patent Application No. 094126981; 7 pages.

* cited by examiner

*Primary Examiner* — Michele M Kidwell
(74) *Attorney, Agent, or Firm* — Morrison & Foerster LLP

(57) ABSTRACT

An interlabial pad capable of reducing the likelihood of falling-off of the pad and leakage of bodily exudates is provided. Making the compression repulsive force from the portion contacting near the vestibule floor to be greater than the compression repulsive force from the portion contacting near the anterior ends of the labia minora pudenda allows a manufacturer to provide an interlabial pad capable of reducing the likelihood of falling-off of the pad and leakage of bodily exudates.

16 Claims, 14 Drawing Sheets

INTERLABIAL PAD

CROSS-REFERENCE TO RELATED APPLICATIONS

This application is based upon and claims the benefit of priority from Japanese Patent application No. 2004-235591 filed on Aug. 12, 2004, the entire contents of which is incorporated herein by reference.

FIELD OF THE INVENTION

The present invention relates to an interlabial pad designed to reduce the likelihood of falling-off of the pad and leakage of bodily exudates.

RELATED ART

Conventionally, a menstrual napkin and tampon have been generally used as a menstrual product. Incidentally, for a menstrual napkin, significant efforts have been taken to prevent menstrual blood from leaking out of a gap due to poor adhesion of napkin to around the ostium vaginae. Also as for a tampon, due to the nature of tampon, a wearer feels, during use of tampon, a foreign object placed inside the wearer's body or discomfort and faces difficulty in inserting the tampon into the ostium vaginae, and therefore various types of tampon products have been proposed to solve these problematic situations.

Under such problematic situations, a menstrual product referred to as an interlabial pad has been recently attracting much attention among menstrual product manufacturers as a menstrual product lying between menstrual napkin and tampon. The interlabial pad is designed for a wearer to wear the pad in such a manner that a part of the entire interlabial pad is sandwiched between the labia of a female wearer and contacts an inner wall of the labia. Thus, the interlabial pad is more adhesive to wearer's body than a menstrual napkin and prevents the leakage of menstrual blood and further blocks the menstrual blood from flowing and touching a large area of the body, thereby allowing a wearer to stay sanitary and clean. Further, the interlabial pad is smaller in size than a menstrual napkin and therefore during use, a wearer feels significantly comfortable and less reluctant to wear the interlabial pad than to wear a tampon which is to be inserted into the vaginae.

To provide an interlabial pad having the above characteristics, interlabial pads having various structures have been developed. For example, Patent document 1 discloses an interlabial pad which is configured so that the pad is folded about the central longitudinal axis of the pad so as to allow one half of the back surface of the pad to face the other half thereof and those two halves of the back surface are attached together at one or more attachment points.

Further, as another known example 1, an interlabial pad comprising a liquid pervious topsheet, a liquid impervious backsheet and an absorbent body interposed therebetween, and designed for a wearer to fold the pad about the central longitudinal axis of the pad for wearing is being sold on approval in the United States over the period from around May 2000 to May 2001 (available from Procter & Gamble Co. Product name Envive).

Moreover, as another known example 2, an interlabial pad has been known in which an absorbent body is covered with a liquid pervious topsheet and front and rear ends of the absorbent body are cut out (available from A-Fem Medical Corp. Product name INSYNC).

[Patent Document 1]: International publication pamphlet WO 02/100315

Incidentally, the term "labia" refers generally to both labia majora pudenda and labia minora pudenda, and the labia majora pudenda are positioned outside the labia minora pudenda near the vestibular floor. Accordingly, portions near the anterior ends of the labia minora pudenda largely open, however, the labia minora pudenda near the vestibule floor are difficult to open because the labia minora pudenda at the above-mentioned point are pushed inside by the right and left labia majora pudenda located outside the labia minora pudenda. Therefore, an interlabial pressure near the vestibular floor is higher than that near the anterior ends of the labia minora pudenda and further the interlabial pressure less fluctuates depending on the wearer's change of position. This trend is always observed irrespective of wearer's body shape.

The interlabial pressure can be measured by using a contact pressure sensor (e.g., available from AMI Techno Co.) and inserting an air-pak equipped inspection device of 12 mm diameter into a space between the labia. For example, in the case of a model having a BMI value(=weight(kg)/height(m)/height(m)) of 19.3 and standing upright with legs astride (i.e., toe spacing of 35 cm), the anterior ends of labia minora pudenda are closed and an interlabial pressure at this point of time in a portion "a" near the vestibular floor is 50 g/cm$^2$ and an interlabial pressure in a portion "b" near the anterior ends of labia minora pudenda is 43 g/cm$^2$ (see FIG. 22). That is, the interlabial pressure in the portion near the vestibular floor is about 1.2 times the interlabial pressure in the portion "b" near the anterior ends of labia minora pudenda. Further, in the case of a model bending down (i.e., toe spacing of 35 cm and lap spacing of 35 cm), the anterior ends of labia minora pudenda of the model are open and the interlabial pressure at this point of time in the portion "a" near the vestibule floor is 12 g/cm$^2$ and the interlabial pressure in the portion "b" near the anterior ends of labia minora pudenda is 0 g/cm$^2$ (see FIG. 23). Thus, in both of the above cases, the interlabial pressure near the vestibular floor is greater than the interlabial pressure near the anterior ends of labia minora pudenda.

On the contrary, an interlabial pad 70 of the known example 1 shown in FIG. 24 is substantially uniform in thickness and in density throughout its entire body. Accordingly, as shown in FIG. 25, when the pad is worn, a portion "A'" of the pad contacting near the vestibular floor where an interlabial pressure is high is more likely to crumple than a portion "B'" of the pad contacting near the anterior ends of labia minora pudenda 20. When the portion "A'" of the pad contacting near the vestibule floor crumples, the anterior ends of labia minora pudenda 20 become open, thereby causing the interlabial pad 70 to more easily fall off and increasing the probability of leakage of bodily exudates.

Further, an interlabial pad 80 of the known example 2 shown in FIG. 26 is comprised of a portion "A'" of the pad contacting near the vestibule floor and a portion "B'" of the pad contacting near the anterior ends of labia minora pudenda and having a thickness greater than that of the portion "A'". Accordingly, as shown in FIG. 27, when the pad is worn, the anterior ends of labia minora pudenda 20 become open. Therefore, the interlabial pad 80 more easily falls off, increasing the probability of leakage of bodily exudates.

In consideration of the above problems, the present invention has been conceived and an object of the invention is to provide an interiabial pad with reduced probability of falling-off of the pad and leakage of bodily exudates.

SUMMARY OF THE INVENTION

The inventors have made an extensive effort to solve the above-mentioned problems. As a result, the inventors have completed the invention based on the fact that making the compression repulsive force from the portion contacting near the vestibular floor greater than the compression repulsive force from the portion contacting near the anterior ends of the labia minora pudenda allows a manufacturer to provide an interlabial pad capable of reducing the likelihood of falling-off of the pad and leakage of bodily exudates. More specifically, the invention provides the followings.

(1) An interlabial pad designed for a wearer to wear the pad so that a portion of the pad near a central longitudinal axis of the pad is aligned with the vestibular floor and at least a part of the pad resides within a labia minora pudenda between labia, the interlabial pad comprising:

an absorbent body for absorbing and retaining body fluids and configured to have a substantially elongated shape extending in its longitudinal and lateral directions;

a first portion contacting near the vestibular floor during use; and a second portion contacting near the anterior ends of the labia minora pudenda during use, a compression repulsive force from the first portion being greater than a compression repulsive force from the second portion.

The interlabial pad described in (1) is characterized in that the compression repulsive force from the first portion is greater than the compression repulsive force from the second portion. The term "compression repulsive force" used herein is intended to mean a compression repulsive force from the pad when the pad is sandwiched between the labia and more specifically, is expressed by a compression force applied to the pad so that a thickness of the pad upon application of a pressure of 0.5 g/cm$^2$ is reduced by 30% of that thickness. Measurement of the compression force can be done using the fabric objective measurement in the form of the Kawabata Evaluation System. According to the interlabial pad of (1), it is assured that even the first portion, to which portion a greater interlabial pressure is applied, is hardly going to crumple and the left/right ends of the labia minora pudenda sandwiching the interlabial pad therebetween remain parallel to each other (see FIG. 1) or are pointing inside a wearer's body (see FIG. 2). Therefore, the likelihood of falling-off of the pad and leakage of bodily exudates is substantially eliminated.

(2) The interlabial pad according to (1), wherein a ratio of the compression repulsive force from the first portion with respect to the compression repulsive force from the second portion is 1.2 to 10.

In the interlabial pad described in (2), the compression repulsive force from the first portion is 1.2 to 10 times the compression repulsive force from the second portion This is based on the fact that as described above, the interlabial pressure applied to the first portion is about 1.2 times the interlabial pressure applied to the second portion. According to the interlabial pad of (2), it is assured that even the first portion, to which portion a greater interlabial pressure is applied, is hardly going to crumple and the left/right ends of the labia minora pudenda sandwiching the interlabial pad therebetween remain parallel to each other (see FIG. 1) or are pointing inside a wearer's body (see FIG. 2). Therefore, the likelihood of falling-off of the pad and leakage of bodily exudates can be effectively reduced.

(3) The interlabial pad according to (1) or (2), wherein a part of the absorbent body in the first portion has greater fiber density than another part of the absorbent body in the second portion.

The interlabial pad described in (3) is characterized in that a part of the absorbent body in the first portion is higher in fiber density than another part of the absorbent body in the second portion. The term "fiber density" used herein is intended to mean a value determined based on the thickness of the pad to which a pressure of 0.5 g/cm2 is being applied and the weight of the pad in case of no pressure applied thereto. According to the interlabial pad of (3), even in the first portion, to which portion a greater interlabial pressure is applied, a distance between fibers in the absorbent body is difficult to decrease and therefore the compression repulsive force from the first portion increases and the interlabial pad is hardly going to crumple. Accordingly, it is assured that the left/right ends of the labia minora pudenda sandwiching the interlabial pad therebetween remain substantially parallel to each other or are pointing inside a wearer's body, thereby effectively reducing the likelihood of falling-off of the pad and leakage of bodily exudates.

(4) The interlabial pad according to any one of (1) to (3), wherein a ratio of the fiber density of the part of the absorbent body in the first portion with respect to the fiber density of another part of the absorbent body in the second portion is 1.2 to 10.

In the interlabial pad described in (4), the ratio of the fiber density of the part of the absorbent body in the first portion with respect to the fiber density of another part of the absorbent body in the second portion is 1.2 to 10. This is based on the fact that the interlabial pressure applied to the first portion is about 1.2 times the interlabial pressure applied to the second portion. According to the interlabial pad of (4), even in the first portion, to which portion a greater interlabial pressure is applied, a distance between fibers in the absorbent body is difficult to decrease and therefore the compression repulsive force from the first portion increases and the interlabial pad is hardly going to crumple. Accordingly, the likelihood of falling-off of the pad and leakage of bodily exudates can be more effectively reduced.

(5) The interlabial pad according to any one of (1) to (4), wherein the part of the absorbent body in the first portion is thicker than another part of the absorbent body in the second portion.

The interlabial pad described in (5) is characterized in that the part of the absorbent body in the first portion is thicker than another part of the absorbent body in the second portion. The term "thickness" used herein is intended to mean a width in the direction of short body axis of the interlabial pad and in the case of an interlabial pad double folded along a central folding line extending along the longitudinal axis of the pad, a width in the direction of short body axis of the interlabial pad being folded. Further, the thickness is the one during application of a pressure of 0.5 g/cm$^2$ to the pad. According to the interlabial pad of (5), the compression repulsive force from the first portion is increased because of the large thickness of that portion and therefore it is assured that the left/right ends of the labia minora pudenda sandwiching the interlabial pad therebetween are pointing inside a wearer's body. Accordingly, the likelihood of falling-off of the pad and leakage of bodily exudates can be effectively reduced.

(6) The interlabial pad according to any one of (1) to (5), wherein a ratio of a thickness of the part of the absorbent body in the first portion with respect to a thickness of another part of the absorbent body in the second portion is 1.2 to 10.

In the interlabial pad described in (6), the ratio of the thickness of the part of the absorbent body in the first portion with respect to the thickness of another part of the absorbent body in the second portion is 1.2 to 10. This is based on the fact that the interlabial pressure applied to the first portion is about 1.2 times the interlabial pressure applied to the second portion. According to the interlabial pad of (5), the compression repulsive force from the first portion is further increased and therefore it is assured that the left/right ends of the labia minora pudenda sandwiching the interlabial pad therebetween are pointing more to the inside of a wearer's body. Accordingly, the likelihood of falling-off of the pad and leakage of bodily exudates can be more effectively reduced.

(7) The interlabial pad according to any one of (1) to (6), wherein the part of the absorbent body in the first portion has fibers disposed thereon and oriented by crossing over the vicinity of the central longitudinal axis of the pad.

The interlabial pad described in (7) is characterized in that the part of the absorbent body in the first portion has fibers disposed thereon and oriented by crossing over the vicinity of the central longitudinal axis of the pad. In the interlabial pad, the fibers of the interlabial pad are oriented in the direction of application of the interlabial pressure and therefore a compression repulsive force from the first portion is increased. Accordingly, it is assured that the left/right ends of the labia minora pudenda sandwiching the interlabial pad therebetween are pointing more to the inside of a wearer's body and consequently the likelihood of falling-off of the pad and leakage of bodily exudates can be more effectively reduced.

(8) The interlabial pad according to any one of (1) to (7), wherein the first portion has an elastic sheet provided therein.

The interlabial pad described in (8) is characterized in that the first portion has an elastic sheet provided therein. That is, the interlabial pad allows a greater compression repulsive force to be applied to the first portion. Accordingly, even when an interlabial pressure is instantaneously changed due to change in wearer's position, the pad instantaneously returns to its original volume, following the opening of the left/right ends of the labia minora pudenda, and the probability of the occurrence of a gap between the inner wall of the labia near the vestibule floor and the interlabial pad is very small. Further, the interlabial pad is able to quickly return to its original volume even after absorption of body fluids. Consequently, the likelihood of falling-off of the pad and leakage of bodily exudates can be more effectively reduced.

(9) The interlabial pad according to any one of (1) to (8), wherein the portion has provided therein an expandable member capable of absorbing water and then increasing a volume of the member.

The interlabial pad described in (9) is characterized in that the first portion has provided therein an expandable member capable of absorbing water and then increasing a volume of the member. When the expandable member absorbs water, the volume of the expandable member is increased, thereby increasing the thickness of the first portion. That is, even in the case of an interlabial pad designed to be thin before use, absorption of body fluids during use of the pad causes the thickness of the first portion to increase, thereby allowing the compression repulsive force from the first portion to increase. Therefore, it is assured that that the left/right ends of the labia minora pudenda sandwiching the interlabial pad therebetween are pointing more to the inside of a wearer's body and consequently the likelihood of falling-off of the pad and leakage of bodily exudates can be more effectively reduced. Further, since the thickness of the interlabial pad before use can be made small, even a person unfamiliar to this kind of interlabial pad is able to easily insert the interlabial pad into an appropriate position corresponding to the narrow interlabial space of the person's body. Moreover, although the interlabial pad is thin and compact before use, the pad will advantageously have a preferable thickness at the time of use.

The invention provides an interlabial pad that allows the labia minora pudenda during use to have a desired form in order to reduce the likelihood of falling-off of the pad and leakage of bodily exudates.

DETAILED DESCRIPTION OF THE PREFERRED EMBODIMENTS

Figure 1:
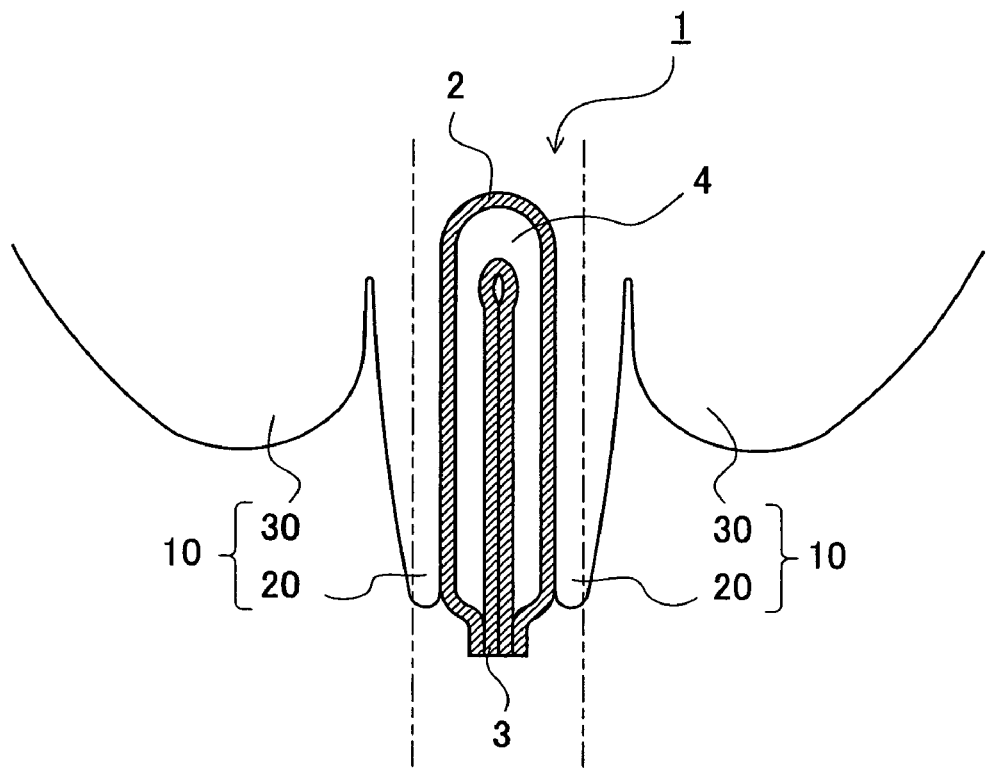
FIG. 1 is a diagram showing the used state of an interlabial pad according to the invention.
Figure 2:
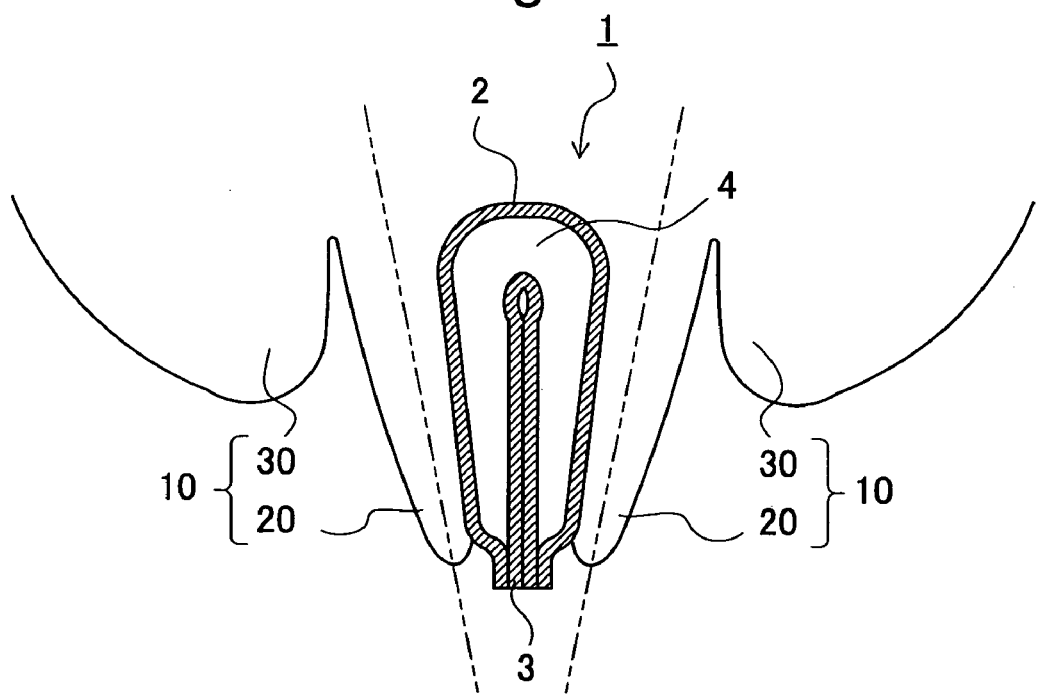
FIG. 2 is a diagram showing the used state of the interlabial pad according to the invention.

Embodiments of the invention will be explained in detail below with reference to accompanying drawings. It should be noted that in the following embodiments other than the first embodiment, explanation of elements used commonly in the first embodiment and the other embodiments will be omitted or simplified. In the drawings of this invention, the first portion is shown as A and the second portion is shown as B.

<First Embodiment>

[Overall Configuration of an Interlabial Pad]

Figure 3:
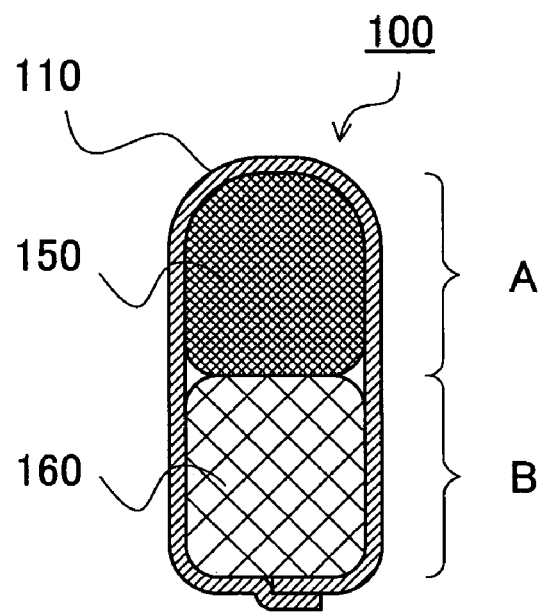
FIG. 3 is a cross-sectional view of the interlabial pad according to the first embodiment, taken along a plane perpendicular to the central longitudinal axis of the pad.

FIG. 3 is a cross-sectional view of an interlabial pad 100 according to the present embodiment, taken along a plane perpendicular to the central longitudinal axis of the pad. As shown in FIG. 3, the interlabial pad 100 according to the invention comprises an absorbent body covered with a topsheet 110, the first portion "A" and the second portion "B". Further, a part of an absorbent body 150 of high fiber density is disposed in the first portion "A" and another part of an absorbent body 160 of low fiber density is disposed in the second portion "B". The topsheet 110 is positioned on wearer's body side during use of the pad (hereinafter, referred to simply as "during use") and pervious to body exudates of a wearer.

Figure 4:
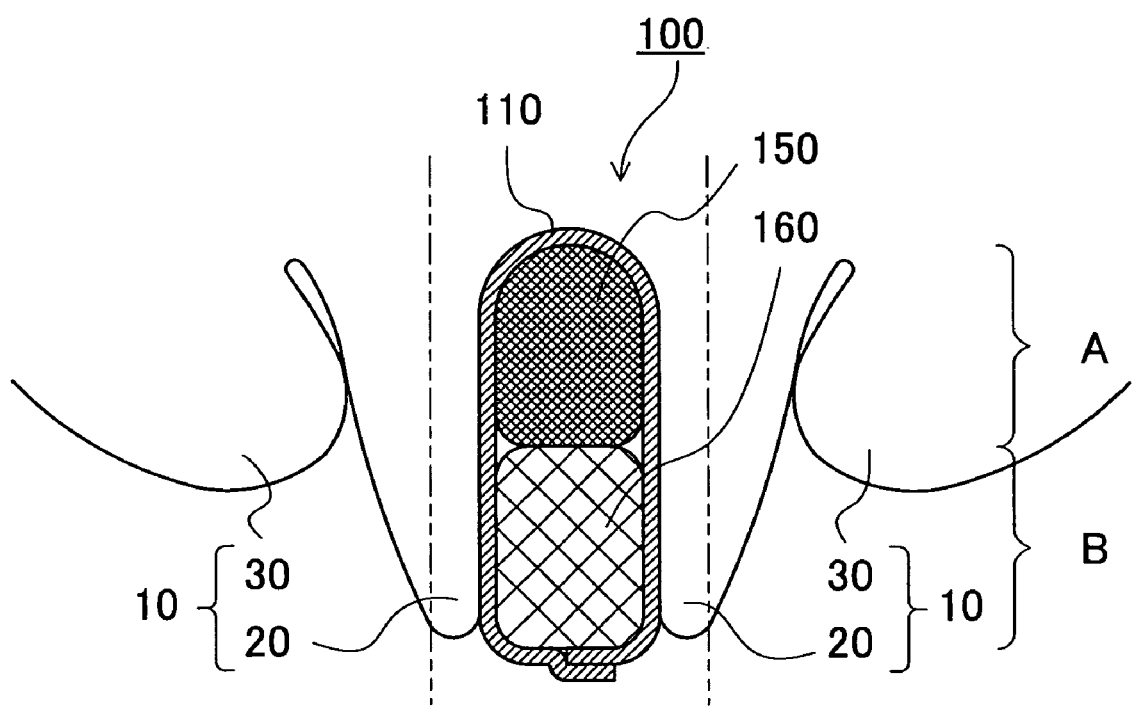
FIG. 4 is a diagram showing the used state of the interlabial pad according to the first embodiment.
Figure 5:
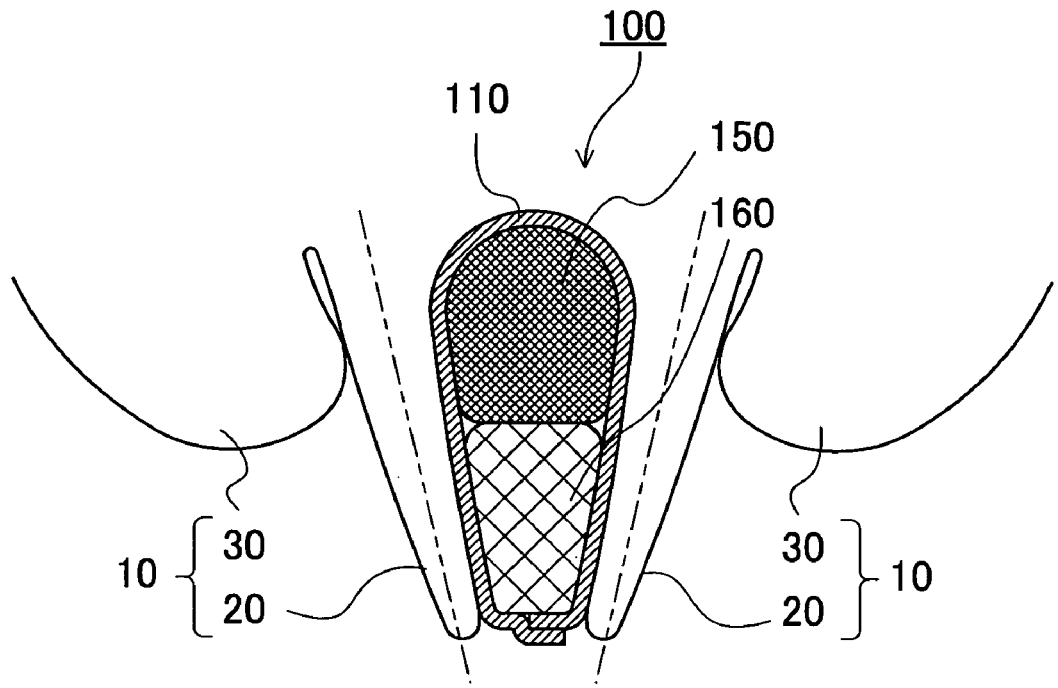
FIG. 5 is a diagram showing the used state of the interlabial pad according to the first embodiment.

FIG. 4 is a diagram showing the used state of the interlabial pad 100 according to the invention. Although during use, larger interlabial pressure is applied to the first portion "A", compression repulsive force from the first portion "A" is greater than that generated in the second portion "B", thereby allowing the labia minora pudenda to keep running almost parallel to each other. In case a difference between compression repulsive forces generated in the first portion "A" and the second portion "B" is increased, the anterior ends of the labia minora pudenda are moved inside, as shown in FIG. 5, thereby more effectively preventing falling-off of the interlabial pad 100 and leakage of bodily exudates.

[Topsheet]

Generally, the topsheet 110 is preferably made of a material that is liquid pervious, hydrophilic and non-irritating to the wearer's skin. Examples of such material include a nonwoven fabric or synthetic nonwoven fabrics made by manufacturing methods, such as point bonding, through-air method, etc. Among those materials, a cellulosic material comprising primarily of hydrophilic fibers is more preferred to prevent a wearer from feeling a foreign object placed inside the wearer's body because of occurrence of displacement between the interlabial pad 100 and inner wall of the labia.

In more detail, nonwoven fabrics manufactured by spun-lacing process and having a thickness of 0.3 mm to 1.0 mm are employed and made in accordance with a method including the steps of: making fibers by mixing 5 to 30 weight percent natural cotton and 70 to 95 weight percent rayon or acetate rayon; preparing the fibers having a specific weight per unit area of 20 g/m² to 50 g/m²; and intertwining the fibers using hydroentanglement and then drying the same. Incidentally, yarns of the fibers are such that when natural cotton is used, a cotton yarn has a length of 15 mm to 60 mm and a fineness of 1.1 dtex to 6.6 dtex, and when rayon or acetate rayon is used, a rayon yarn has a length of 25 mm to 51 mm and a fineness of 1.1 dtex to 6.6 dtex. Further, films with permeable holes or sheets made by lamination of films on layers of fibers (i.e., lamination finishing) may be employed.

[Absorbent Body]

The part of the absorbent body 150 disposed in the first portion "A" is higher in fiber density than another part of the absorbent body 160 disposed in the second portion "B". More specifically, the ratio of the fiber density of another part of the absorbent body 160 with respect to the density of the part of the absorbent body 150 is preferably in the range of 1.2 to 10 and more preferably in the range of 1.5 to 10.

In more detail, the fiber density of the part of the absorbent body 150 is preferably in the range of 0.011 g/cm³ to 2.000 g/cm³ and more preferably in the range of 0.020 g/cm³ to 1.000 g/cm³. Further, the fiber density of another part of the absorbent body 160 is preferably in the range of 0.001 g/cm³ to 1.670 g/cm³ and more preferably in the range of 0.002 g/cm³ to 0.833 g/cm³. It should be noted that an absorbent body whose fiber density decreases stepwise from the first portion "A" to the second portion "B" may be employed.

The absorbent body is made up of a material or mixture of materials, such as pulp, chemical pulp, rayon, acetate, natural cotton, absorbent polymer, absorbent polymer fibers, synthetic fibers, etc., and may be comprised of fibers coated with oil or containing oil. The fibers may be manufactured so that sheet-type fibers are made by manufacturing methods, such as airlaid method, spun-lacing process, papermaking method, melt blowing process, etc., and then the sheet-type fibers are processed by an embossing treatment, i.e., passed between rolls having the shape of needle ring, dot, grid, wave, etc. Incidentally, an embossed area ratio is preferably of 0.1% to 60% and more preferably of 1% to 30%.

The fineness of fibers used in the absorbent body 150 disposed in the first portion "A" is relatively smaller than the fineness of fibers used in the absorbent body 160 disposed in the second portion "B", or the fiber length of the former is relatively shorter than that of the latter. Further, the amount of fibers used in the absorbent body 150 may be relatively increased to be greater than the amount of fibers used in the absorbent body 160 and the fibers used in these absorbent bodies may be subjected to embossing treatment, etc., in order to make the thickness of the entire absorbent body substantially uniform.

Attachment between the absorbent body 150 and topsheet 110 may be provided by using well-known techniques such as adhesives or bonding by pressing a salient of embossment. An adhesive coating pattern is applied through processes such as spiral coating, controlled-seam coating, coater coating, curtain coater coating, spray gun coating, etc., however, among those coating methods, the spray gun coating is preferred since it allows a pitch between attachment portion and non-attachment portion to be smaller. Preferably, an adhesive has a specific weight per unit area of 1 g/m² to 30 g/m² and more preferably has a specific weight per unit area of 3 g/m² to 10 g/m². Further, in the case of an adhesive coating pattern applied in the shape of a line, the diameter of the line is preferably in the range of 30 μm to 300 μm. When the adhesive has a specific weight per unit area not greater than 1 g/m² or the diameter of the line is not greater than 30 μm, the adhesive is confined between the fibers making up the topsheet 110 comprising a fiber assembly, thus causing resultant bonding force acting between the absorbent body and topsheet to be reduced. On the other hand, when the adhesive has a specific weight per unit area not less than 30 g/m² or the diameter of the line is not less than 300 μm, the perimeter becomes hardened. Although portions of the absorbent body and topsheet to which adhesives are to be applied are not particularly limited, it is preferred that the adhesives are applied to at least locations between the absorbent body and topsheet. Examples of an embossing pattern may include, but not limited to, grid-, dot-, wave-like patterns, etc. Also, portions to be bonded by pressing a salient of embossment are not particularly limited, however, when a backsheet is employed, it is preferred that the topsheet 110 and backsheet extending along the perimeter of the absorbent body 150 are both bonded by pressing the salient of embossment.

[First Portion "A" and Second Portion "B"]

The average length of labia minora pudenda is about 14 mm, although it depends on individual women. Accordingly, the first portion "A" can be formed so as to correspond to a portion of the labia ranging from a reference site contacting the vestibule floor to a site at a depth of 7 mm from the reference site in the vertical downward direction. Further, the second portion "B" can be formed so as to correspond to the remaining portion of the labia (i.e., a portion of the labia not corresponding to the portion "A"). For example, in the case of an interlabial pad, where during use, the backsheet is folded about the central longitudinal axis of the pad so that two halves of the backsheet face each other, the first portion "A" can be formed in a portion of the pad covering a distance of up to 7 mm in both outward directions from the central longitudinal axis of the pad and the second portion "B" can be formed a portion of the pad covering a distance of from 7 mm to 14 mm in both outward directions from the central longitudinal axis of the pad. For example, even more than three portions having three different magnitudes of compression repulsive force are formed in the interlabial pad, a portion of the pad to be placed closest to the vestibule floor is the fist portion "A" and a portion of the pad to be placed closest to the anterior ends of labia minora pudenda is the second portion "B".

Moreover, the average value of the length of labia minora pudenda is 55 mm, i.e., and 50 mm in the forward direction and 5 mm in the rearward direction from ostium vaginae. Accordingly, a portion of the interlabial pad sandwiched between labia in the longitudinal direction of the pad is within a distance of up to 50 mm in the forward direction and a distance of up to 5 mm in the rearward direction from a position of the pad contacting the ostium vaginae. Additionally, since the front side of labia minora pudenda is longer and thicker than the rear side thereof, an interlabial pressure generated by the front side is higher than that generated by the rear side. Therefore, in consideration of the above fact, compression repulsive forces generated in the portions of the pad may be adjusted. That is, the interlabial pad may be formed so that compression repulsive force from the first portion "A" is made larger on the front side than on the rear side.

[Other Configuration of Interlabial Pad]

The interlabial pad 100 may be configured to include at least an absorbent body capable of absorbing and retaining menstrual blood and the configuration of the pad is not particularly limited. For example, an absorbent body only, the configuration that an absorbent body is covered with a liquid pervious topsheet 110, or the configuration that the absorbent body sandwiched between a liquid pervious topsheet 110 and a liquid impervious backsheet is folded along a fold line of the pad. Further, the shape of the interlabial pad 100 is not particularly limited, as long as the interlabial pad 100 is appropriately shaped so as to fit to the female's labia, i.e., the pad is shaped into ellipse, gourd, dew, or the like. That is, the interlabial pad may be configured so that, during use, the entire interlabial pad resides within the interlabial space of a female wearer or a part of the pad is exposed to the out of the labia. The interlabial pad preferably has a total outside dimension of 40 mm to 180 mm and more preferably 80 mm to 130 mm in its longitudinal direction. Further, the pad preferably has a total outside dimension of 20 mm to 100 mm and more preferably 50 mm to 80 mm in its thickness direction.

[Slit Processing]

In the first portion "A", a slit may be provided in a direction crossing over the central longitudinal axis of the interlabial pad. In this case, an external pressure applied to a part of the interlabial pad 100 is difficult to act on the other part of the pad. That is, an external pressure applied to the first portion "A" is divided by the slit, thereby making it difficult for the pressure to transmit to the other portion of the pad. More specifically, perforation slits having a slit length of 5 mm to 20 mm and a slit pitch of 5 mm to 20 mm may be formed in the absorbent body 150 in a zigzag pattern in a direction crossing over the central longitudinal axis of the interlabial pad.

[Mini-Sheet Piece]

In the case of an interlabial pad of the type which is folded about a fold line along the central longitudinal axis of the interlabial pad so as to allow one half of the back surface of the pad to face the other half thereof, a Mini-sheet piece may be formed so as to cross over those two halves of the back surface. In this case, an opening through which a finger may be inserted is formed between the Mini-sheet piece and the back surface, thereby allowing a wearer to accurately place the interlabial pad in an appropriate position of the wearer's body. The Mini-sheet piece can be formed to have the same configuration as those of the topsheet and backsheet. Further, the Mini-sheet piece may be formed using a lamination of layers of elastic fibers, films, a foamed material containing air cells, etc.

Examples of elastic fibers include fibers made from a thermoplastic material alone, such as polyethylene, polypropylene, polyethylene telephthalate or fibers made from such thermoplastic material and having a sheath-core configuration, sheath-core configuration but with the core shifted off-center, or side-by-side configuration. Among those fibers, fibers which are formed using a mechanical crimping tool or formed so that latent helical crimp is activated by heat treating to develop fine and firm crimps, called secondary crimps, are preferred because of their elasticity. In consideration of elasticity or comfort during use, the fineness of the fiber is preferably in the range of 0.5 dtex to 8.8 dtex and the length of the fiber is preferably in the range of 3 mm to 64 mm. The thickness of the fiber is preferably in the range of 0.2 mm to 3.0 mm and more preferably in the range of 0.5 mm to 1.5 mm. Films may be made from materials which is molded out of elastic polyethylene, polypropylene, polyethylene telephthalate resins, and highly elastic urethane, rubber, etc., by injection molding of a single material, or synthetic or composite materials using a T-shaped film die or inflation film molding machines. The foamed material may be made by foaming elastic resin such as polyethylene, polypropylene, highly elastic urethane, rubber, or made from a cellulose sponge having absorbency. Incidentally, the foamed material may be either continuous or discontinuous type.

Examples of a non-woven fabric made from elastic fibers will be described. A non-woven fabric obtained through-air method made by preparing a laminate of fiber by carding, bonded by melting thermoplastic fibers, is preferably utilized due to its superiority in repulsive elasticity. Non-woven fabrics can be formed using many processes such as, for example, point bonding, spun bonding and spunlace processes, which have been commonly utilized. Further, non-woven fabrics could be fabrics including layers of spun-bonded fibers which are formed by spinning continuous filaments and bonding the filaments to the hot embossing film or could be SMS (spunbond/meltblown/spunbond) non-woven fabrics which are formed by meltblowing the fibers and then bonding the meltblowing fibers to spunbond fibers. Also, non-woven fabrics could be made by chemical bonding processes in which fibers are laminated and binder is applied to the surface of the lamination to bond the fibers, or by airlaid processes. The non-woven fabrics may be made from the above materials in a single form or made by laminating the above materials, one on top of another, and bonding the materials with an adhesive or embossing adhesive. Further, the non-woven fabrics may be preferably made from a material whose repulsive force or thickness is adjusted by an embossing pattern.

[Individual Wrapping Body for Interlabial Pad]

The interlabial pad 100 may be contained in an individual wrapping body. The individual wrapping body can be formed from a material having a thickness of 15 μm to 60 μm and made from polyethylene, polypropylene, polyethylene terephthalate, polyvinyl alcohol, poly lactic acid, polybutyl succinate, or non-woven fabrics, paper, etc., or a lamination of the above materials. In more detail, the wrapping body can be formed of a film made by mixing 0 weight percent to 80 weight percent of low-density polyethylene resin and 20 weight percent to 100 weight percent of high-density polyethylene resin, and preparing a mixture of the above resins so as to allow the film to have a specific weight per unit area of 15 g/m$^2$ to 35 g/m$^2$. Moreover, the wrapping body can be formed of a film that is drawn to enhance the orientation of the resin. Examples of non-woven fabrics include spunbond non-woven fabrics, point-bond non-woven fabrics, through-air non-woven fabrics, etc., and in this case, those fabrics may be water-repellent. Among those non-woven fabrics, SMS (spunbond/meltblown/spunbond) non-woven fabrics composed of ultra-fine fibers and comprising meltblown fibers whose inter-fiber distance is vary small are preferred. In this case, preferably, a spunbond layer has a basic weight range of 5 g/m$^2$ to 15 g/m$^2$, a meltblown layer has a basic weight range of 1 g/m$^2$ to 10 g/m$^2$, and a spunbond layer has a basic weight range of 5 g/m$^2$ to 15 g/m$^2$. Further, the individual wrapping body is preferably made from a material that does not permit the transmission of the color of menstrual blood being absorbed or may be formed by mixing between 0.2 weight percent and 10 weight percent of pigment into the body, or may be printed with ink. Moreover, the interlabial pad and individual wrapping body may be made from a flushable material that collapses upon wet loading or a biodegradable material.

[Compression Repulsive Force]

A compression repulsive force can be measured using the Kawabata Evaluation System—, i.e., KES-5 HANDY-TYPE COMPRESSION TESTER available from Kato Tech Co, Ltd under the condition that a pressure connector having a surface area of 2 cm$^2$ moves at a speed of 0.1 cm/sec alternately toward and away from a fabric sample, compressing the sample. The interlabial pad can be tested using Kawabata Evaluation System as long as the size of the interlabial pad can be determined so as to accommodate the size of the pressure connector and therefore the size of the pad is not particularly limited. In the case of an interlabial pad of the type which is folded along a fold line along the central longitudinal axis of the interlabial pad during use so as to allow two halves of the backsheet to face each other, the pad in a folded state is placed on a table for measurement. The term "compression repulsive force" used in the invention is intended to mean a compression repulsive force measured when the pad is sandwiched between the labia and more specifically, a compression force applied to the pad so that the thickness of the pad upon application of a pressure of 0.5 g/cm$^2$ is reduced by 30% of the thickness.

Figure 21:
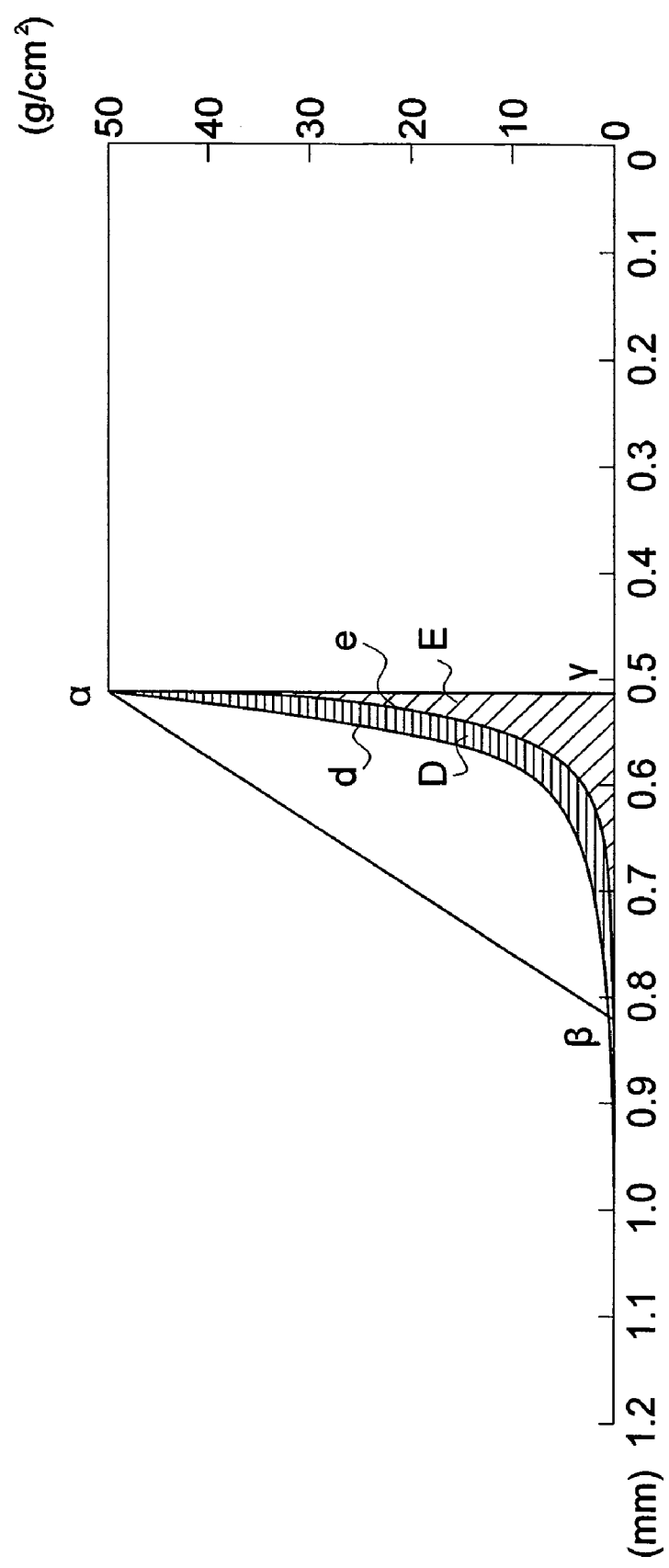
FIG. 21 is an illustration of compression characteristics of the interlabial pad, measured using Kawabata Evaluation System.
Figure 22:
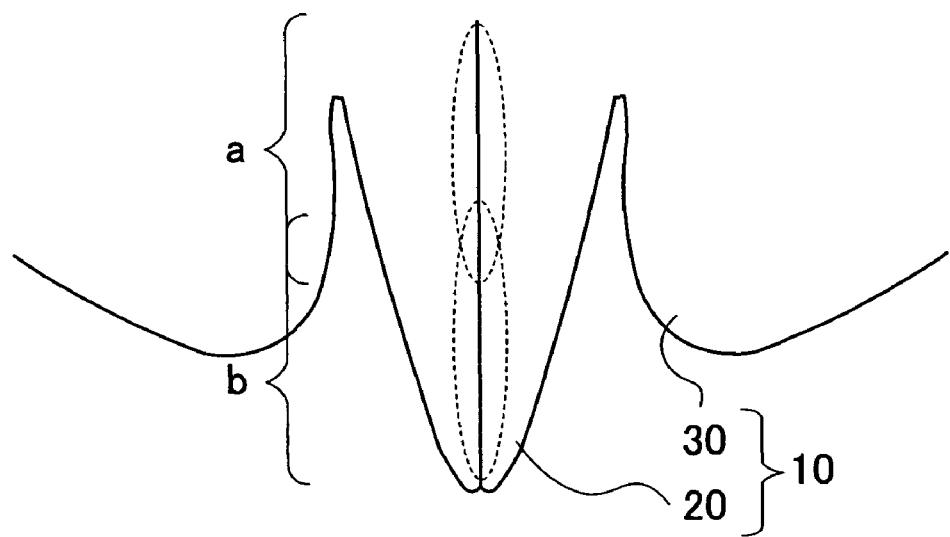
FIG. 22 is an illustration of how the labia of a wearer standing upright with legs astride appear.
Figure 23:
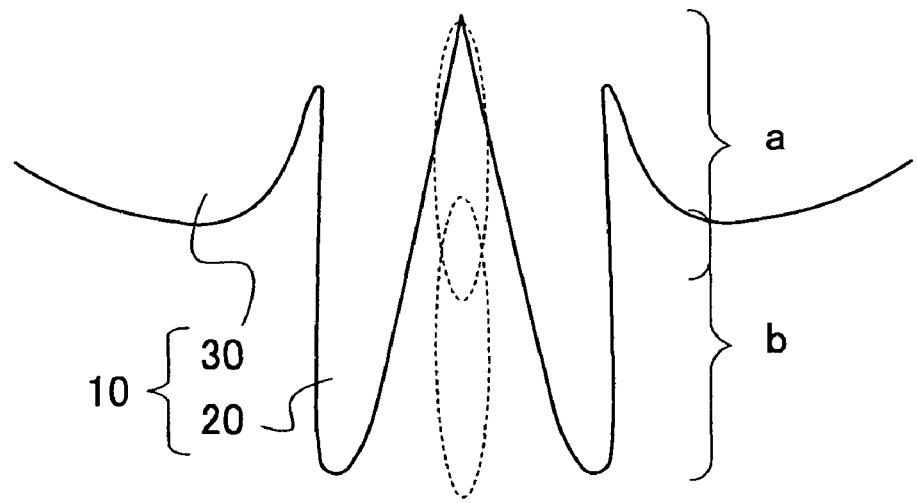
FIG. 23 is an illustration of how the labia of a wearer bending down appear.

FIG. 21 illustrates the compression characteristics measured using Kawabata Evaluation System. The abscissa axis indicates the thickness (mm) of a sample upon application of a pressure and the vertical axis indicates a pressure (g/cm$^2$) applied to the sample. The curve "d" in FIG. 21 represents a relationship between the gradually increasing pressure applied to the sample and the thickness of the sample, and the curve "e" represents a relationship between the gradually releasing pressure applied to the sample and the thickness of the sample. Accordingly, a compression repulsive force can be determined so that the thickness of the sample to which a pressure of 0.5 g/cm$^2$ is applied is read as a reference thickness and then a pressure applied to the sample to cause the thickness of the sample to be reduced by 30% of the reference thickness is read from FIG. 21.

Figure 17:
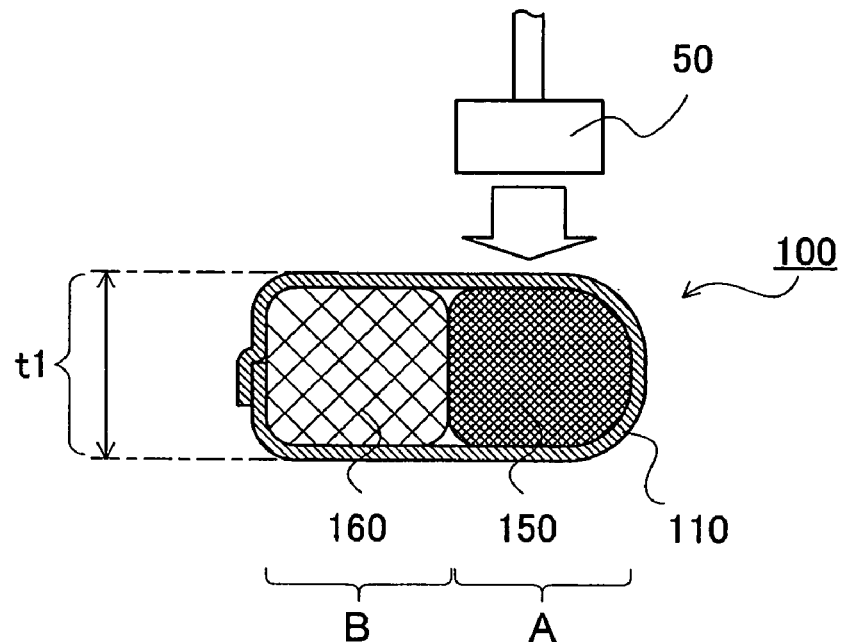
FIG. 17 is an illustration of how to measure the compression repulsive force from the interlabial pad.
Figure 18:
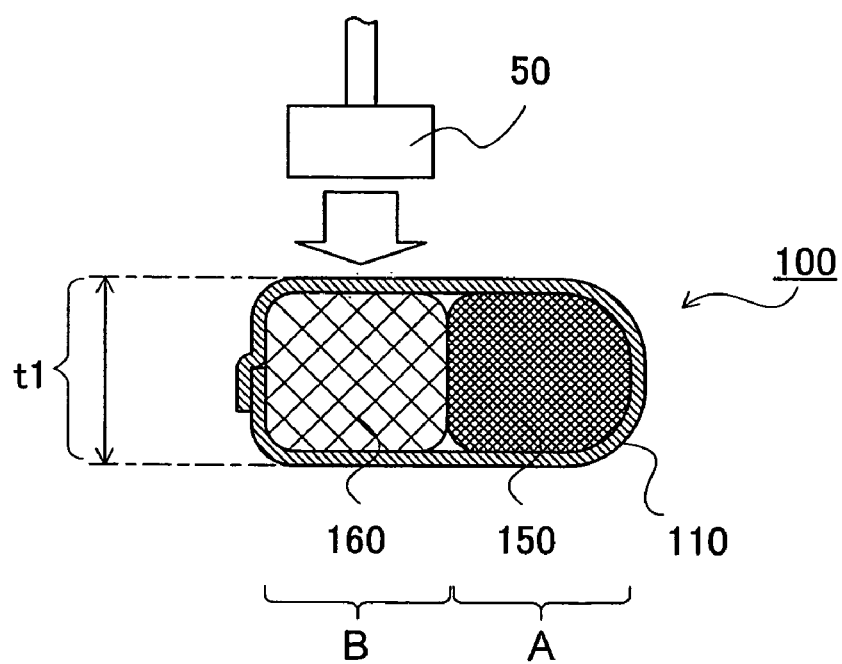
FIG. 18 is an illustration of how to measure the compression repulsive force from the interlabial pad.
Figure 19:
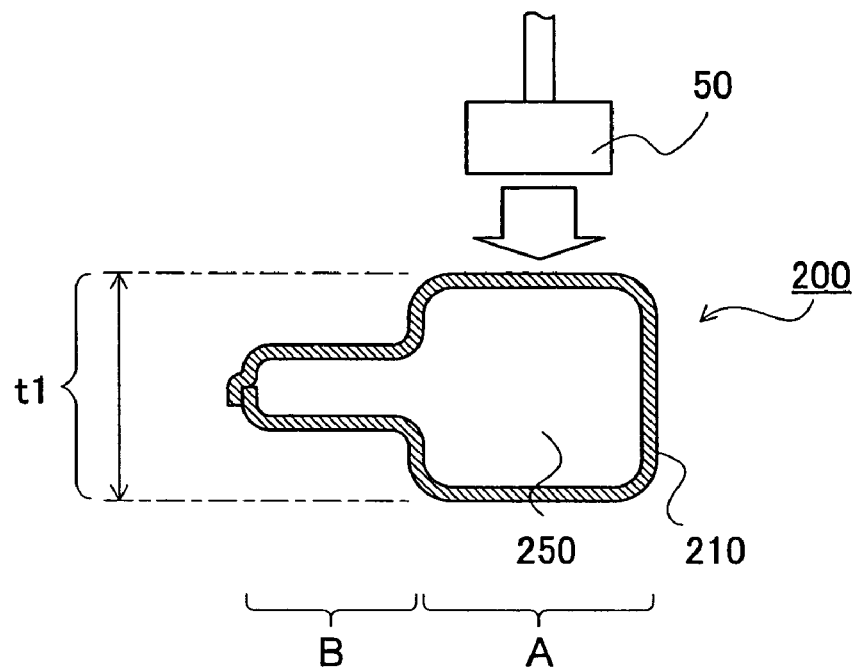
FIG. 19 is an illustration of how to measure the compression repulsive force from the interlabial pad.
Figure 20:
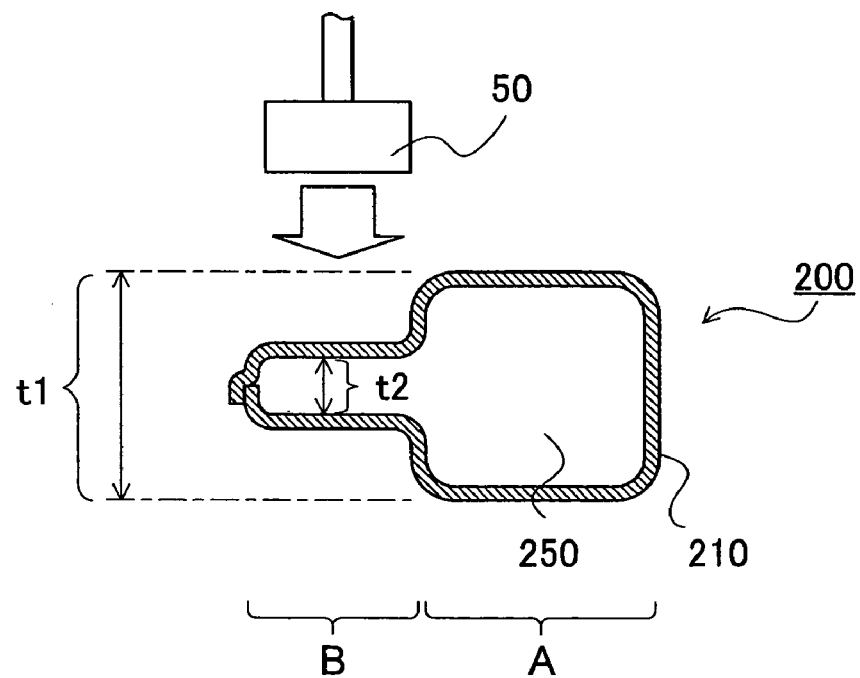
FIG. 20 is an illustration of how to measure the compression repulsive force from the interlabial pad.

It should be noted that how to measure a compression repulsive force varies depending on the shape of an interlabial pad. First, in case an interlabial pad has no uneven surface on the side of the topsheet, the compression repulsive force from the first portion "A" is a compressive force which is determined by reading beforehand as a reference thickness the thickness "t1" of the pad to which a pressure of 0.5 g/cm$^2$ is applied and then measuring a pressure applied to the pad to cause the thickness of the pad to be reduced by 30% of the reference thickness (refer to FIG. 17). Further, the compression repulsive force from the second portion "B" is a compressive force which is determined by measuring a pressure applied to the pad to cause the thickness of the pad to be reduced by 30% of the reference thickness t1 (refer to FIG. 18). On the other hand, in case an interlabial pad has uneven surface on the side of the topsheet, the compression repulsive force from the first portion "A" is a compressive force which is determined by measuring a pressure applied to the pad to cause the thickness of the pad to be reduced by 30% of the reference thickness t1 (refer to FIG. 19). However, the compression repulsive force from the second portion "B" is a compressive force which is determined by measuring a pressure applied to the pad to cause the thickness of the pad to be reduced by 30% of the reference thickness t1, rather than t2 (refer to FIG. 20). That is, the compressive force is not a force which is determined by measuring a pressure applied to the pad to cause the thickness of the pad to be reduced by 30% of the actual thickness t2, but a force which is determined by measuring a pressure applied to the pad to cause the thickness of the pad to be reduced by 30% of an apparent thickness (i.e., thickness t1 of the first portion). In this manner, a difference in compression repulsive forces due to a difference in thicknesses can be precisely measured. Accordingly, in case an absorbent body is provided only in the first portion "A" and a thickness difference between the first portion "A" and the second portion "B" is extremely large, the pressure connector at the time of measurement of compression repulsive force on the second portion "B" moves only a distance equal to 30% of the reference thickness t1 of the first portion "A" and is not brought into contact with the second portion "B". Therefore, the compression repulsive force from the second portion "B" becomes zero.

[Second Embodiment]

Figure 6:
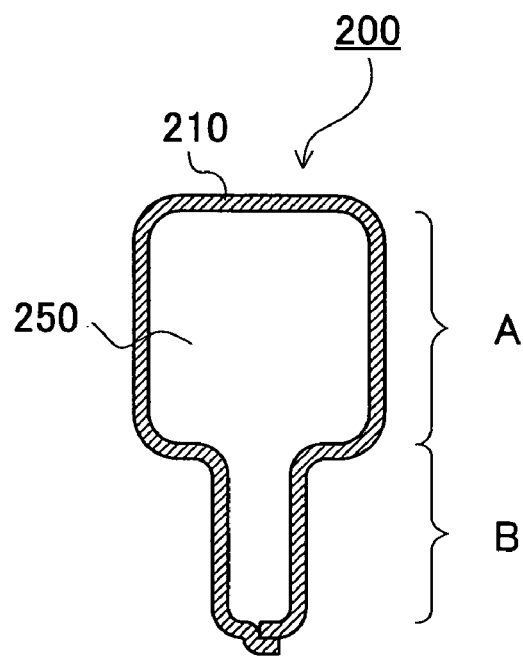
FIG. 6 is a cross-sectional view of the interlabial pad according to the second embodiment, taken along a plane perpendicular to the central longitudinal axis of the pad.

An interlabial pad 200 according to this embodiment is characterized in that an absorbent body 250 in the first portion "A" is thicker than the absorbent body 250 in the second portion "B". The remaining configuration of the embodiment is similar to that of the first embodiment. FIG. 6 is a cross sectional view of the interlabial pad 200, taken along a plane perpendicular to the central longitudinal axis of the pad. The thickness of the absorbent body 250 in the first portion "A" is preferably 1.2 to 10 times the thickness of the absorbent body 250 in the second portion "B". In more detail, the thickness of the absorbent body 250 in the first portion "A" is preferably in the range of 2 mm to 20 mm and more preferably in the range of 3 mm to 15 mm. Further, the thickness of the absorbent body 250 in the second portion "B" is preferably in the range of 0.5 mm to 17 mm and more preferably in the range of 1 mm to 12.5 mm. It should be noted that the absorbent body 250 may be formed so that the thickness of the body from the first portion "A" to the second portion "B" is reduced to be thin stepwise.

Figure 7:
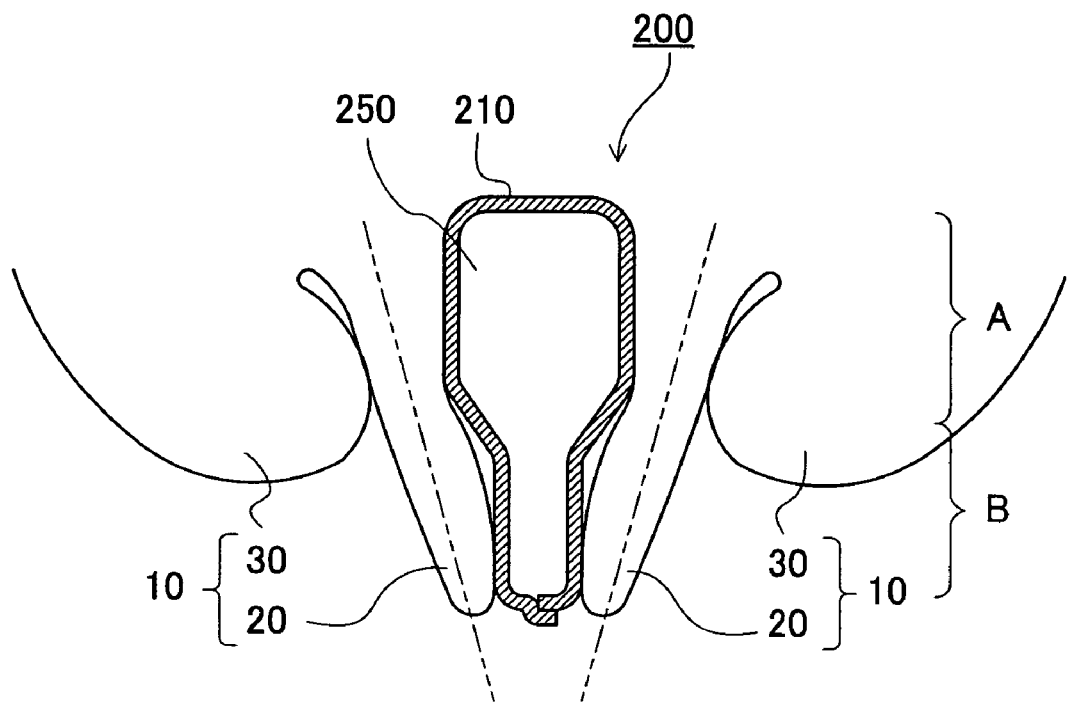
FIG. 7 is a diagram showing the used state of the interlabial pad according to the second embodiment.

FIG. 7 is a diagram showing the used state of the interlabial pad 200 according to the embodiment. In comparison with the absorbent body before use of the pad, the absorbent body 250 in the first portion "A" is slightly compressed by application of an interlabial pressure to the absorbent body. However, even during use, the absorbent body 250 in the first portion "A" remains thicker than the absorbent body 250 in the second portion "B" and the ends of labia minora pudenda interpose the interlabial pad therebetween while pointing inside the wearer's body. Accordingly, this effectively prevents the falling off of the interlabial pad 200 and leakage of bodily exudates.

[Modification 1]

Figure 8:
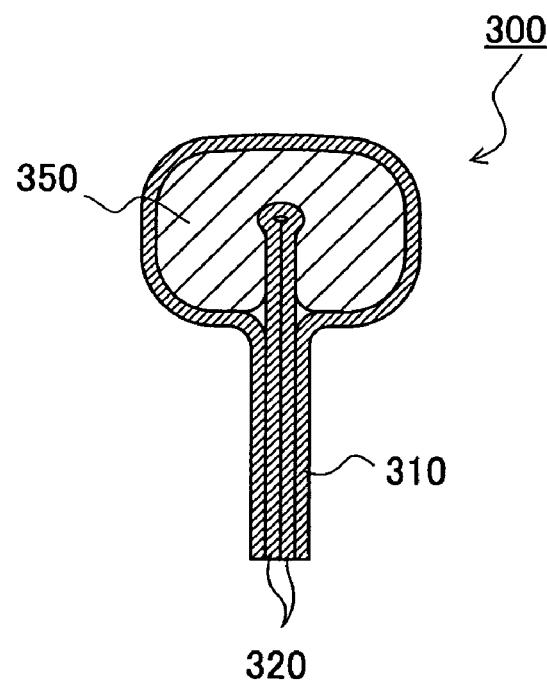
FIG. 8 is a cross-sectional view of the interlabial pad according to the modification 1 of the second embodiment, taken along a plane perpendicular to the central longitudinal axis of the pad.

As shown in FIG. 8, an interlabial pad 300 according to a modification 1 of the embodiment comprises a liquid pervious topsheet 310 as well as a liquid impervious backsheet 320, in which an absorbent body 350 is provided only in the first portion "A". Further, the absorbent body 350 is disposed between the topsheet 310 and the backsheet 320. The interlabial pad 300 is worn in such a manner that the pad is folded about a fold line along the central longitudinal axis of the pad so as to cause the two halves of the backsheet 320 to face each other.

[Backsheet]

The backsheet is formed of a liquid impervious and moisture permeable material to lower the humidity during use. For example, the backsheet can be formed from a material having a thickness of 15 μm to 60 μm and made from polyethylene, polypropylene, polyethylene telephthalate, polyvinyl alcohol, poly lactic acid, polybutyl succinate, non-woven fabrics, paper, etc., or a lamination of the above materials. Further, the backsheet may be formed of an air permeable film which is made by incorporating inorganic fillers in a film and drawing the film.

In more detail, the backsheet can be formed from a film made primarily from low-density polyethylene (LDPE) resin and having a pore diameter of 0.1 mm to 0.6 mm, a basic weight of 15 g/m² to 35 g/m², an open pore area percentage of 10% to 30%. Moreover, examples of non-woven fabrics include spunbond non-woven fabrics, through-air non-woven fabrics, point-bond non-woven fabrics, etc., and in this case, those fabrics may be water-repellent. Among those non-woven fabrics, SMS (spunbond/meltblown/spunbond) non-woven fabrics composed of ultra-fine fibers and containing meltblown fibers whose inter-fiber distance is vary small are preferred. In this case, preferably, a spunbond layer has a basic weight range of 5 g/m² to 15 g/m², a meltblown layer has a basic weight range of 1 g/m² to 10 g/m², and a spunbond layer has a basic weight range of 5 g/m² to 15 g/m².

In the modification 1, since only the second portion "B" is not provided with the absorbent body 350, the absorbent body 250 in the first portion "A" is able to remain thicker than the absorbent body 250 in the second portion "B" even during use. Accordingly, even during use, the ends of labia minora pudenda are able to continue to point inside the wearer's body, thereby effectively preventing falling-off of the interlabial pad 300 and leakage of bodily exudates.

[Modification 2]

Figure 9:
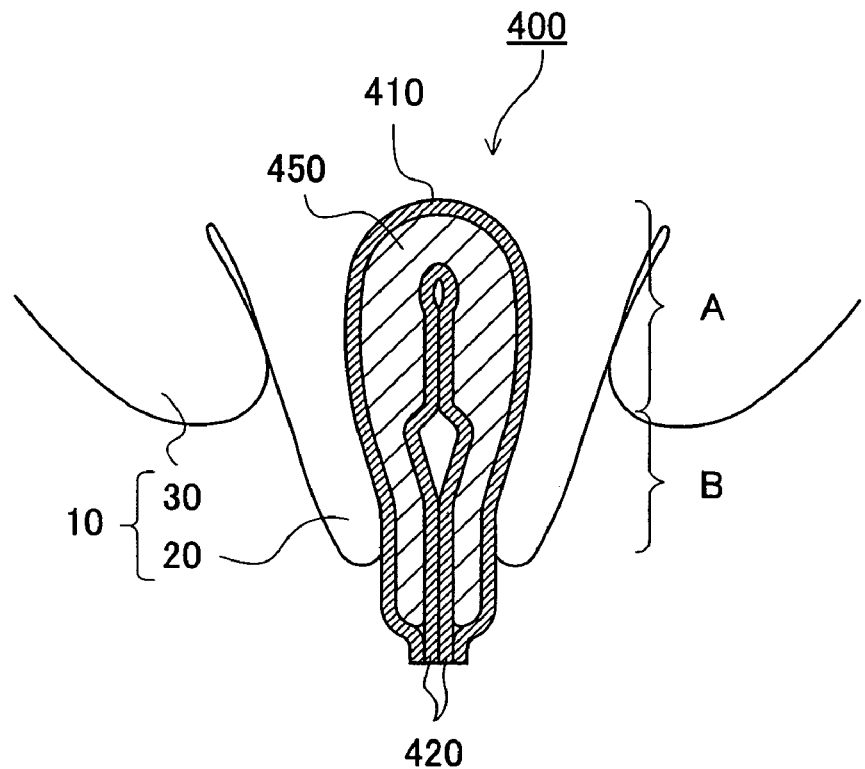
FIG. 9 is a diagram showing the used state of the interlabial pad according to the modification 2 of the second embodiment.

FIG. 9 is a diagram showing the used state of an interlabial pad 400 according to a modification 2 of the embodiment. The interlabial pad 400 is configured so that in the interlabial pad 300 according to the modification 1, the second portion "B" also has an absorbent body 450 provided therein and the absorbent body 450 in the first portion "A" protrudes to the side of a backsheet 420. The absorbent body 450 in the first portion "A" could be a lamination of two or more absorbent bodies. In this case, an absorbent body disposed over the interlabial pad 200 is used as an upper absorbent body and an absorbent body provided only in the first portion "A" and protruding to the side of the backsheet 420 is used as a lower absorbent body. For example, taking into account that a wearer is highly sensitive to foreign substance near the vestibule floor, a flexible absorbent body is used as the upper absorbent body whereas an absorbent body capable of absorbing large quantities of body fluids and retaining the same is used as the lower absorbent body. In this case, the fiber density of the upper absorbent body is preferably in the range of 0.03 g/cm³ to 0.1 g/cm³ and the thickness thereof is preferably in the range of 1 mm to 15 mm. Further, the density of the lower absorbent body is preferably in the range of 0.05 g/cm³ to 0.2 g/cm³ and the thickness thereof is preferably in the range of 1 mm to 10 mm.

More specifically, the upper absorbent body can be formed using a method including the steps of: preparing rayon, finished so as to have a fiber length of 51 mm, a crimp ratio of 50%, a 0.2 weight percent of hydrophilic oil attached thereto, and a fineness of 3.3 dtex; mixing 60 weight percent to 100 weight percent rayon and 0 weight percent to 50 weight percent natural cotton; and blending, opening and depositing the mixture on a collecting surface to form an airlaid web with a specific weight per unit area of 180 g/m². Further, the lower absorbent body can be formed using a method including the steps of: preparing a pulp having a fiber length of 1 mm to 8 mm; preparing fibers made from 100 weight percent pulp; and depositing the fibers on a collecting surface to form an airlaid web with a specific weight per unit area of 400 g/m². After attachment of the upper absorbent body to the lower absorbent body, the first portion "A" and the second portion "B" are processed by an embossing treatment that uses embossing rolls with different embossed area ratios. In more detail, an embossed area ratio for the first portion "A" is 0.1% and an embossed area ratio for the second "B" is 0.5%. A slit may be formed in those absorbent bodies to provide flexibility to the absorbent bodies.

In the interlabial pad 400 according to the modification 2, uneven surface on the topsheet 410 due to a thickness difference between the first portion "A" and the second portion "B" are hardly likely to occur, thereby allowing the interlabial pad to easily attach to the inner wall of the labia. Accordingly, this more effectively prevents falling-off of the interlabial pad 400 and leakage of bodily exudates.

[Modification 3]

An interlabial pad according to a modification 3 of the embodiment is characterized in that the material of fibers used in the first portion "A" is more bulky than the material of fibers used in the first portion "B". In this manner, using a bulky material only in an absorbent body in the first portion "A" allows the first portion "A" to be thicker than the second portion "B". Accordingly, this more effectively prevents falling-off of the interlabial pad and leakage of bodily exudates.

Examples of a bulky material include rayon or acetate with embossed patterns and a material made primarily from crimp-processed chemical pulp cross-linked with cross-linking agent. Further, examples of such bulky material include a material made primarily from composite synthetic fibers having a sheath-core configuration in which crimp is developed by differential thermal contraction of resin such as polyethylene, polypropylene, polyethylene telephthalate, a sheath-core configuration but with the core shifted off-center, and a side-by-side configuration. The above materials may be drawn during spinning process to enhance the orientation of molecules or may include materials having different cross sections such as Y-type and C-type cross sections.

[Modification 4]

An interlabial pad according to a modification 4 of the embodiment is characterized in that the amount of fibers used in the first portion "A" is substantially equal to the amount of fibers used in the second portion "B" and both the portions are processed by an embossing treatment to have different embossed area ratios. In more detail, an embossed area ratio for an absorbent body in the first portion "A" is made smaller than an embossed area ratio for an absorbent body in the second portion "B". Accordingly, the first portion "A" is thicker than the second portion "B", thereby effectively preventing falling-off of the interlabial pad and leakage of bodily exudates.

[Third Embodiment]

An interlabial pad according to this embodiment is characterized in that fibers oriented to cross over the vicinity of the central longitudinal axis of the interlabial pad are disposed in an absorbent body in the first portion "A". The remaining configuration of the embodiment is similar to that of the first embodiment. In the interlabial pad according to the embodiment, the fibers are oriented in the direction of action of interlabial pressure and therefore stiffness of the fibers act to cause a compression repulsive force to be larger in the first portion "A". Accordingly, this more effectively prevents falling-off of the interlabial pad and leakage of bodily exudates. Further, even when the interlabial pad is compressed by interlabial pressure, but when the pressure is released, the fibers return to its original shape and the absorbent body also returns to its original thickness.

The method for disposing fibers so as to allow the fibers to orient in a direction crossing over the vicinity of the central longitudinal axis of the interlabial pad includes a method for controlling the orientation of fibers when fibers are deposited on a collecting surface. More specifically, a fiber assembly before opening of fibers is loaded in a fiber opening system and the fibers after opening are deposited as a fiber assembly on a conveyer belt and then transferred to the subsequent treatment units. In this case, right after opening of fibers, the speed of fibers is added with a collection speed which is determined primarily by a suction force generated by a suction system provided on the mesh-like/inner surface of the conveyer belt. Further, immediately upon collection on the conveyer belt, the speed of a fiber assembly is added with the speed of the conveyer belt. Accordingly, increasing the collection speed greater relative to the speed of the conveyer belt allows partial control of the orientation of the fiber assembly.

[Modification 1]

An interlabial pad according to a modification 1 of the embodiment is characterized in that the absorbent body in the first portion "A" is processed by an embossing treatment and the orientation of fibers is controlled by an embossing pattern. The embossing pattern includes, but not limited to, a pattern allowing fibers to orient so as to cross over the vicinity of the central longitudinal axis of the interlabial pad, such as dot-, grid-, and wave-like patterns. Among those patterns, a dot-like embossing pattern providing flexibility is preferred in consideration of comfort.

More specifically, the absorbent body in the first portion "A" comprises a fiber assembly having a pattern of embossments formed thereon, which pattern is made up of a set of zigzag dots to have an embossed ratio of 0.5%, a pin diameter of 1.0 mm, and a pitch of 12.5 mm. Fibers adjacent to the pattern made up of a set of zigzag dots formed by an embossing treatment are pushed into a direction crossing over the vicinity of the central longitudinal axis of the interlabial pad and then bonded by thermal welding. The fibers in the absorbent body in the first portion "A" are thus oriented in a direction crossing over the vicinity of the central longitudinal axis of the interlabial pad. This correspondingly causes a compression repulsive force to be greater in the first portion "A" and effectively prevents falling-off of the interlabial pad and leakage of bodily exudates. Incidentally, the pattern made up of a set of zigzag dots preferably has an embossed area ratio of 0.3% to 60%.

[Modification 2]

An interlabial pad according to a modification 2 of the embodiment is characterized in that an absorbent body in the first portion "A" is needled in a direction crossing over the vicinity of the central longitudinal axis of the interlabial pad. Needling of the absorbent body in the first portion "A" using the needle punching method, etc., allows the fibers to orient in a direction crossing over the vicinity of the central longitudinal axis of the interlabial pad and prevents falling-off of the interlabial pad and leakage of bodily exudates.

[Modification 3]

An interlabial pad according to a modification 3 of the embodiment is characterized in that an absorbent body in the first portion "A" is streamed with water so as to allow water flow in a direction crossing over the vicinity of the central longitudinal axis of the interlabial pad. For example, the fibers of the absorbent body in the first portion "A" can be hydroentangled using the spunlace process, etc., while the fibers are oriented in the direction crossing over the vicinity of the central longitudinal axis of the interlabial pad. This correspondingly causes a compression repulsive force to be greater in the first portion "A" and prevents falling-off of the interlabial pad and leakage of bodily exudates.

[Fourth Embodiment]

Figure 10:
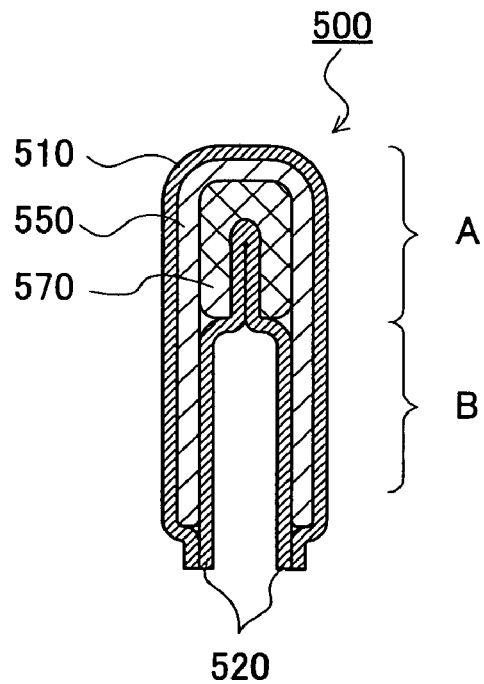
FIG. 10 is a cross-sectional view of the interlabial pad according to the fourth embodiment, taken along a plane perpendicular to the central longitudinal axis of the pad.

An interlabial pad 500 according to this embodiment is characterized in that the first portion "A" has an elastic sheet 570 provided therein. The remaining configuration of the embodiment is similar to that of the first embodiment. FIG. 10 illustrates a cross-sectional view of the interlabial pad 500 according to the embodiment, taken along a plane perpendicular to the central longitudinal axis of the pad. As shown in FIG. 10, the elastic sheet 570 is provided symmetrical to the central longitudinal axis of the pad.

Figure 11:
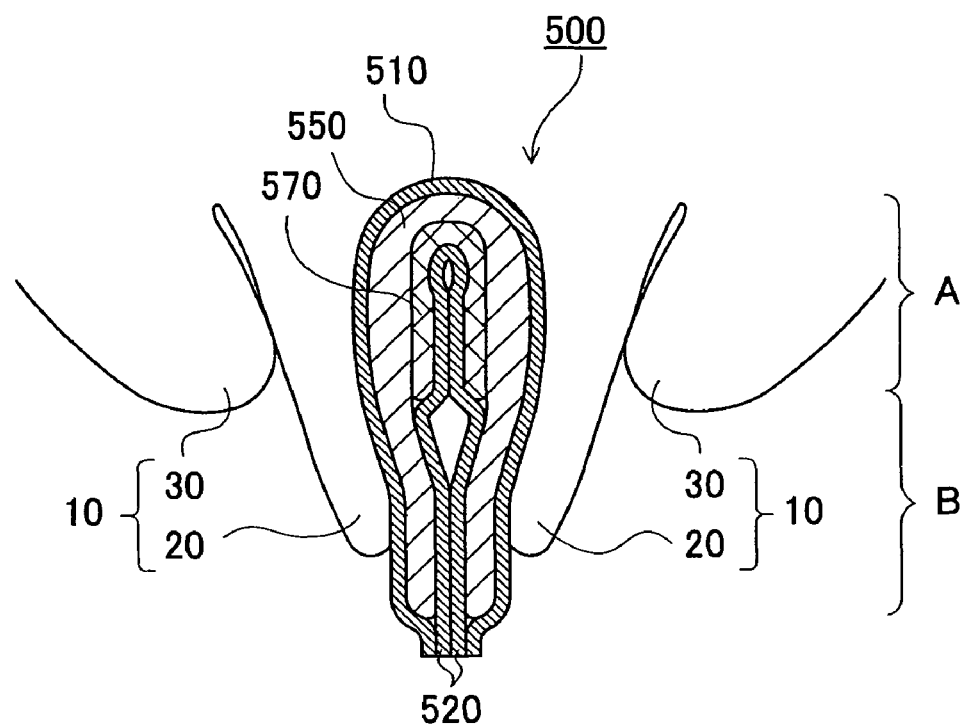
FIG. 11 is a diagram showing the used state of the interlabial pad according to the fourth embodiment.

FIG. 11 is a diagram showing the used state of the interlabial pad 500. A high interlabial pressure is applied to the first portion "A" and provided with the elastic sheet 570 and thus the pad in the first portion "A" is compressed. However, the first portion "A" is able to remain thicker than the second portion "B", thereby allowing the anterior ends of the labia minora pudenda to securely point inside a wearer's body. Accordingly, this effectively prevents falling-off of the interlabial pad and leakage of bodily exudates.

Figure 12:
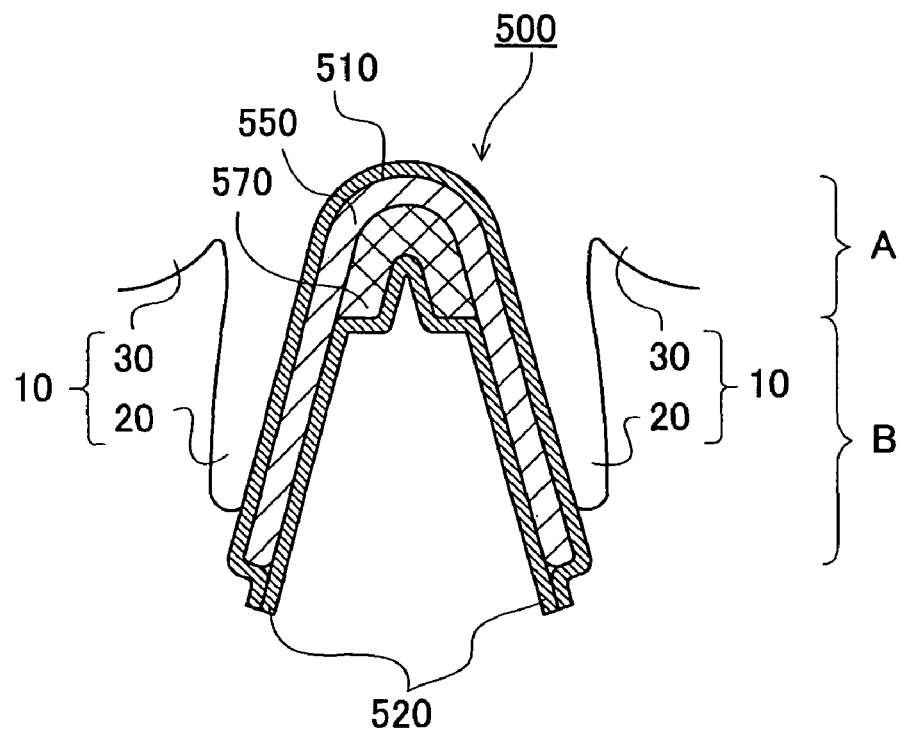
FIG. 12 is a diagram showing the used state of the interlabial pad according to the fourth embodiment.

Furthermore, how the interlabial pad 500 looks like such as when a wearer stands up from a chair, causing a space between the anterior ends of the labia minora pudenda of the wearer to become slightly larger, is shown in FIG. 12. The first portion "A" and provided with the elastic sheet 570 returns to its original volume at the moment of reduction of the interlabial pressure and therefore the probability of the occurrence of a gap between the inner wall of labia near the vestibule floor and the interlabial pad 500 is very small. Accordingly, regardless of wearer orientation, falling-off of the interlabial pad 500 and leakage of bodily exudates can be effectively prevented.

Where the elastic sheet 570 is to be disposed is not particularly limited as long as the sheet is symmetrical to the central longitudinal axis of the pad. In the case of the elastic sheet 570 formed from a material having an affinity to body fluids, the elastic sheet may be provided either on the side of the topsheet 510 facing the wearer's body during use, between the topsheet 510 and the absorbent body 550, or between the absorbent body 550 and the backsheet 520. Further, in the case of the elastic sheet 570 formed from a material having no affinity to body fluids, the elastic sheet may be provided either between the absorbent body 550 and the backsheet 520 or on the side of the backsheet 520 opposite the wearer's body during use. Among those configurations of the interlabial pad, the elastic sheet is preferably provided between the absorbent body 550 and the backsheet 520 in consideration of affinity with body fluids and comfort during use.

In the case of an interlabial pad of the twofold type, the elastic sheet 570 may be provided so as not to cross over the central longitudinal axis of the pad, however, when the elastic sheet 570 is provided so as to cross over the central longitudinal axis of the pad, a strong force acting when the pad is folded causes the pad to return to its original state and therefore a compression repulsive force from the first portion "A" can be increased. In order to reduce wearer's physical discomfort due to inclusion of foreign substance, the elastic sheet 570 may be provided with perforation slits placed along a folding axis of the elastic sheet.

The size of the elastic sheet 570 is not particularly limited; however, when taking into account the flexibility of the interlabial pad, it is preferably not greater than the size of the absorbent body 550. Also, the thickness of the elastic sheet 570 is not particularly limited; however, it is preferably in the range of 1 mm to 10 mm. When the thickness of the elastic sheet is within the above range, a flexible interlabial pad can be obtained which is characterized in that the ratio of the compression repulsive force from the first portion "A" with respect to the compression repulsive force from the second portion "B" is in the range of 1.2 to 10.

The elastic sheet 570 may be formed from a lamination of layers of elastic fibers, films, a foamed material with air cells, etc. Examples of elastic fibers include fibers made from thermoplastic material alone, such as polyethylene, polypropylene, polyethylene telephthalate, or fibers having a sheath-core configuration, sheath-core configuration but with the core shifted off-center, or side-by-side configuration, in which thermoplastic materials are used. Among those fibers, fibers which are formed using a mechanical crimping tool or formed so that heat-treating, called secondary crimps, are preferred because of their elasticity. In consideration of elasticity or comfort during use, the fineness of the fiber is preferably in the range of 0.5 dtex to 8.8 dtex and the length of the fiber is preferably in the range of 3 mm to 64 mm. Films may be made from materials which is molded out of elastic polyethylene, polypropylene, polyethylene telephthalate resins, and highly elastic urethane, rubber, etc., by injection molding of a single material, or synthetic or composite materials using a T-shaped film die or inflation film molding machines. The foamed material may be made by foaming elastic resin such as polyethylene, polypropylene, highly elastic urethane, rubber, or made from a cellulose sponge for high absorbency of various liquid types. Incidentally, the foamed material may be either continuous or discontinuous.

Examples of a non-woven fabric made from elastic fibers will be described. A non-woven fabric made by carding and laminating webs, and bonding webs by melting thermoplastic fibers (called through-air bonding) is advantageous because of its repulsive elasticity and preferably utilized. Non-woven fabrics can be formed using many processes such as, for example, point bonding, spun bonding and spunlace processes, which have been commonly utilized. Further, non-woven fabrics could be fabrics including layers of spunbonded fibers which are formed by spinning continuous filaments and bonding the filaments by a hot embossing treatment or could be SMS (spunbond/meltblown/spunbond) non-woven fabrics which are formed by meltblowing the fibers and then bonding the meltblowing fibers to spunbond fibers. Also, non-woven fabrics could be made by chemical bonding processes in which fibers are laminated and binder is applied to the surface of the lamination to bond the fibers, or by airlaid processes. The non-woven fabrics may be made from the above materials in a single form or made by laminating the above materials, one on top of another, and bonding the materials with an adhesive or fixing in embossing treatment. Further, the non-woven fabrics may be preferably made from a material whose compressability or bulk-restoring force in a predetermined direction is adjusted by an embossing pattern.

[Fifth Embodiment]

Figure 13:
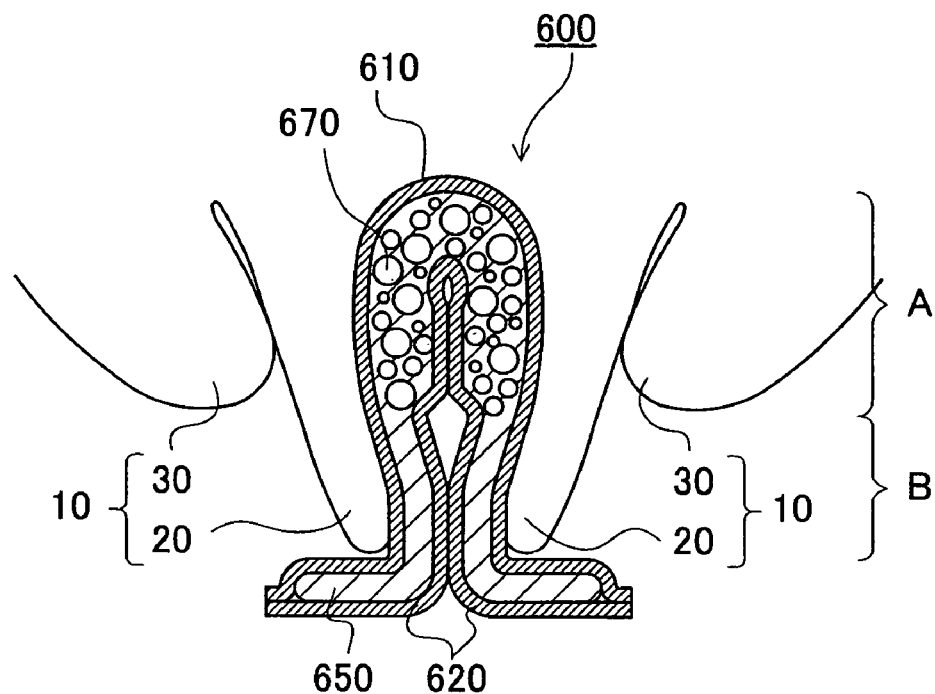
FIG. 13 is a diagram showing the used state of the interlabial pad according to the fifth embodiment.

An interlabial pad 600 according to this embodiment is characterized in that the first portion "A" has an expandable member 670 provided therein. FIG. 13 is a diagram showing the used state of the interlabial pad 600 according to this embodiment. As shown in FIG. 13, the expandable member 670 can be disposed within an absorbent body 650 residing between a topsheet 610 and a backsheet 620. The expandable member 670 is a member capable of absorbing moisture and then increasing its volume. That is, the expandable member 670 absorbs body fluids such as viscid fluid, menstrual blood, urine, sweat, etc., and then increases its volume, thereby increasing its thickness. Accordingly, the interlabial pad 600 during use becomes thicker in the first portion "A" than in the second portion "B", thereby reducing the likelihood of falling-off of the interlabial pad and substantially eliminating the probability of leakage of bodily exudates.

The expandable member 670 include, but not particularly limited to, a material capable of absorbing an amount of water approximately not less than 10 times its own weight and then increasing its volume to at least 1.5 times its original volume, and preferably to not less than 3 times its original volume. Such material is made from, for example, absorbent polymer, absorbent polymer fibers, fiber bands made out of super compressed fibers, cellulose sponge, etc. More specifically, the above material is made from, for example, saponified starch-polyacrylic grafted polymer, starch polyacrylate-grafted polymer, cross-linked cellulose or cellulose graft polymer, saponified acrylic acid polymer, saponified polyethylene oxide, carboxymethyl cellulose, polyvinyl acetate, polyacrylic acid sodium, etc. Further, the expandable member may also be composed of fiber bands having water soluble binder applied thereto, such as polyvinyl alcohol, alkylcellulose, carboxymethyl cellulose, gelatin, etc.

The expandable member 670 may be disposed as an absorbent body itself within the absorbent body 650 as long as the member 670 is provided in the first portion "A", or may be provided between the topsheet 610 and the absorbent body 650 or between the absorbent body 650 and the backsheet 620, or otherwise within the topsheet 610. Further, the expandable member 670 may be covered with a covering member. In this case, the covering member is preferably stretching so as not to prevent the expandable member 670 from expanding. The covering member could be fine wave-like crape tissue, spunlaced non-woven fabrics made by non-woven processing employing water jet punch method in which water jet pressure is lowered to increase the tensile strength and elongation of yarn, films or non-woven fabrics processed by an embossing treatment to have a wave embossed pattern.

Figure 14:
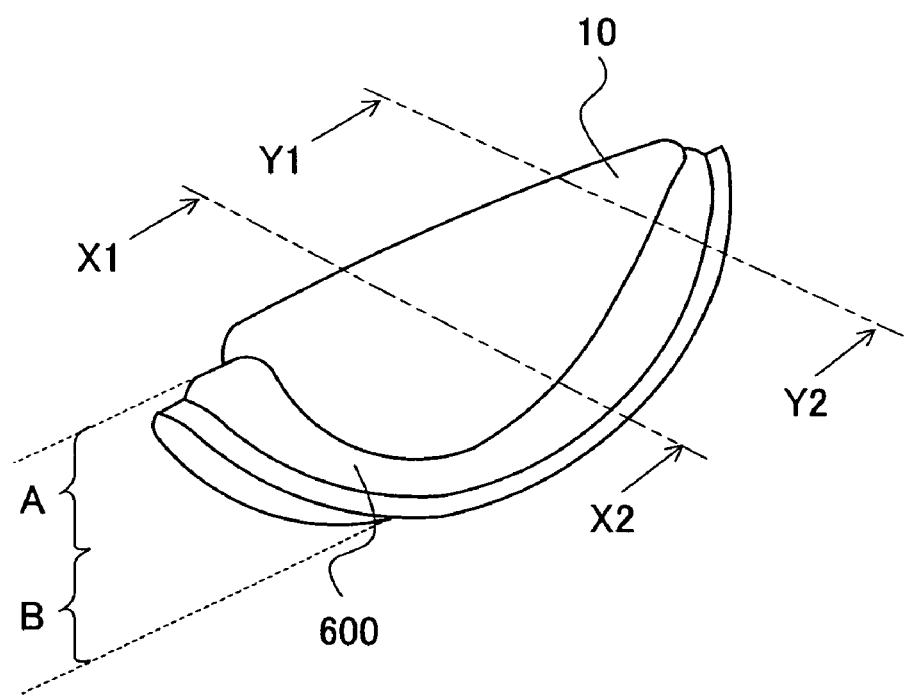
FIG. 14 is a diagram showing the used state of the interlabial pad according to the fifth embodiment.
Figure 15:
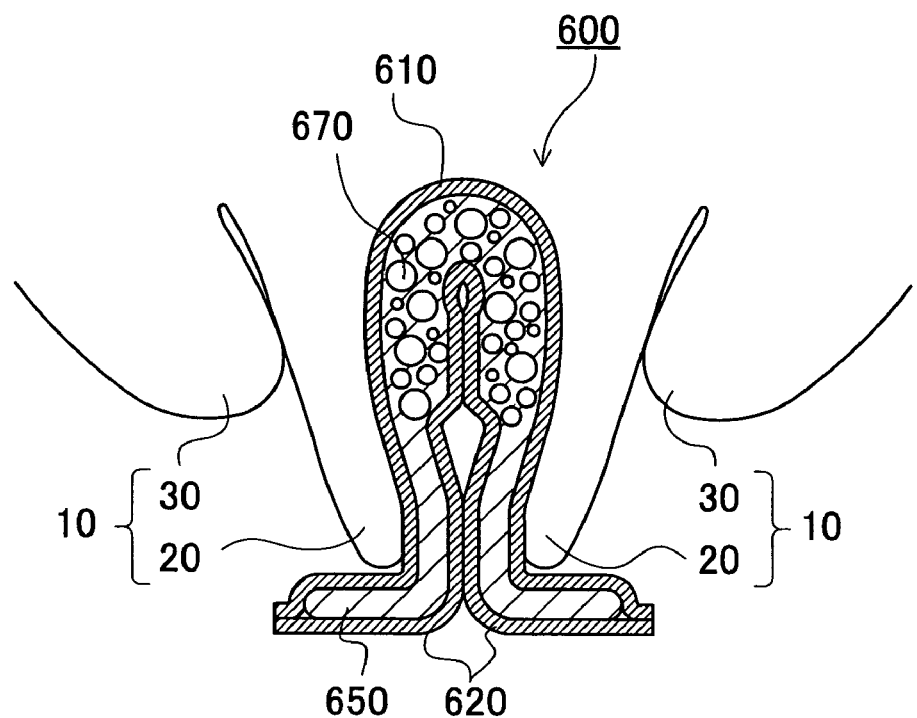
FIG. 15 is a cross-sectional view taken along line X1-X2 of FIG. 14.
Figure 16:
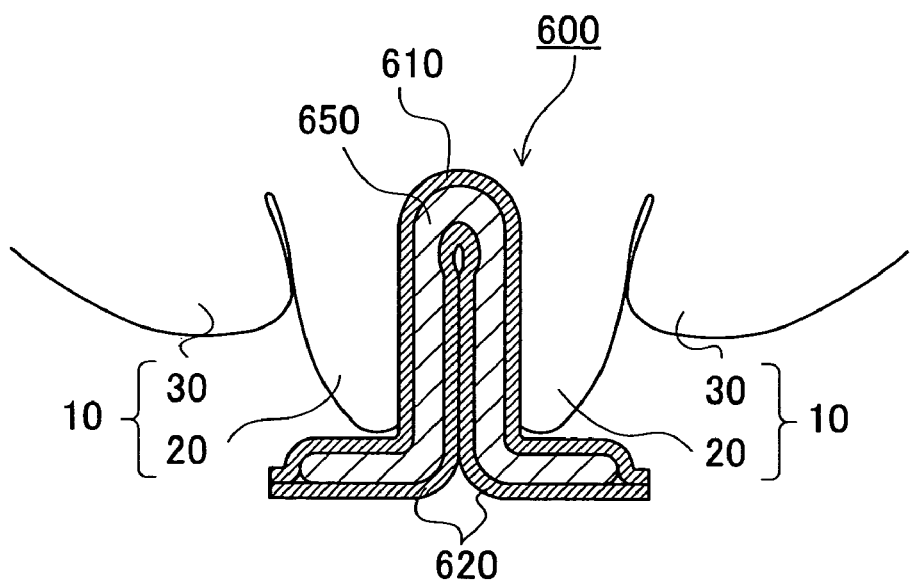
FIG. 16 is a cross-sectional view taken along line Y1-Y2 of FIG. 14.

FIG. 14 is a diagram showing the used state of the interlabial pad 600 according to the embodiment. Further, FIG. 15 is a cross-sectional view taken along line X1-X2 of FIG. 14 and FIG. 16 is a cross-sectional view taken along line Y1-Y2 of FIG. 14. The X1-X2 cross-sectional view is a cross-sectional view of the front side of labia and the Y1-Y2 cross-sectional view is a cross-sectional view of the rear side of labia. As appears respectively from these FIGS., the expandable member 670 is disposed within the absorbent body 650 in the X1-X2 cross-sectional views, whereas the expandable member 670 is not disposed in the Y1-Y2 cross-sectional views. As noted here, the interlabial pad may be formed so that the expandable member 670 is disposed only in a portion of the pad contacting the front side of labia rather than in a portion of the pad contacting the rear side thereof.

EXAMPLES

Example 1

An example 1 of an interlabial pad shown in FIG. 3 was formed which has the shape of a rectangular parallelepiped and comprises the absorbent body whose fiber density is higher in the first portion "A" than in the second portion "B". More specifically, the absorbent body in the first portion "A" and the absorbent body in the second portion "B" were both formed from 100 weight percent pulp having a fiber length of 1 mm to 8 mm. Incidentally, different methods were used for formation of those two portions. In more detail, the absorbent body in the first portion "A" was formed by garnetting so that fibers are opened using an airlaid process, and collected by a suction force so as to allow the fibers to have a specific weight per unit area of 700 g/m$^2$. On the other hand, the absorbent body in the second portion "B" was formed by garnetting so that fibers are opened using the airlaid process and collected by a suction force so as to allow the fibers to have a specific weight per unit area of 300 g/m$^2$. Then, the absorbent body was processed by an embossing treatment that uses embossing rolls having a dot pattern of embossments formed thereon with an embossed area ratio of 0.5%, in order to make the thicknesses of the first portion "A" and the second portion "B" substantially equal to each other.

Example 2

An example 2 of an interlabial pad shown in FIG. 6 was formed which has the shape of a rectangular parallelepiped and comprises the absorbent body that is thicker in the first portion "A" than in the second portion "B". More specifically, the absorbent body in the first portion "A" and the absorbent body in the second portion "B" were both formed from fibers similar to those used in the Example 1. The absorbent bodies in the two portions were both formed by garnetting so that fibers are opened using an airlaid process, and collected by a suction force so as to allow the fibers to have a specific weight per unit area of 700 g/m$^2$. Then, the first portion "A" and the second portion "B" were processed by an embossing treatment that used embossing rolls having different patterns of embossments and different embossed area ratios for the individual portions. That is, the embossed area ratios for the first portion "A" was set to 0.5%, and the embossed area ratios for the second portion "B" was set to 10%, respectively, in order to make the second portion "B" substantially smaller in thickness than the first portion "A".

Example 3

An example 3 of an interlabial pad of the twofold type shown in FIG. 9 was formed so that only an absorbent body in the first portion "A" protrudes toward the backside of the pad, thereby allowing the pad to have a double-layered structure. More specifically, one absorbent body disposed over the interlabial pad was used as an upper absorbent body and the other absorbent body provided only in the first portion "A" and disposed between the upper absorbent body and the backsheet was used as a lower absorbent body. In more detail, the upper absorbent body was formed from fibers, which are made by mixing 85 weight percent rayon having a fiber length of 51 mm, a crimp ratio of 50%, a 0.2 weight percent of hydrophilic oil attached thereto and a fineness of 3.3 dtex, and 15 weight percent natural cotton. The upper absorbent body was formed by garnetting so that fibers are opened using an airlaid process, and collected by a suction force so as to allow the fibers to have a specific weight per unit area of 180 g/m$^2$. On the other hand, the lower absorbent body was formed from 100 weight percent pulp having a fiber length of 1 mm to 8 mm. The lower absorbent body was formed by garnetting so that fibers of the pulp are opened using the airlaid process and collected by a suction force so as to allow the fibers to have a specific weight per unit area 400 g/m$^2$. Then, the lower absorbent body was superimposed onto the upper absorbent body and the first portion "A" and the second portion "B" was processed by an embossing treatment that used embossing rolls having different patterns of embossments and different embossed area ratios for the individual portions. That is, the embossed area ratios for the first portion "A" was set to 0.1% and the embossed area ratios for second portion was set to 0.5%, respectively, in order to make the second portion "B" substantially smaller in thickness than the first portion "A".

[Comparative Sample 1]

Figure 24:
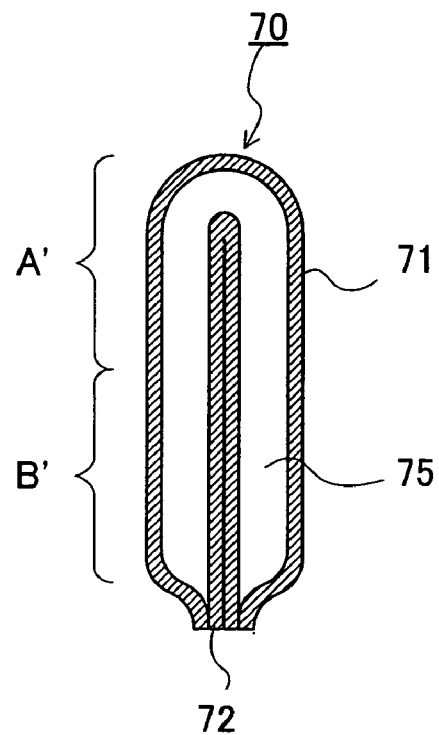
FIG. 24 is a cross-sectional view of the interlabial pad according to the known example 1, taken along a plane perpendicular to the central longitudinal axis of the pad.
Figure 25:
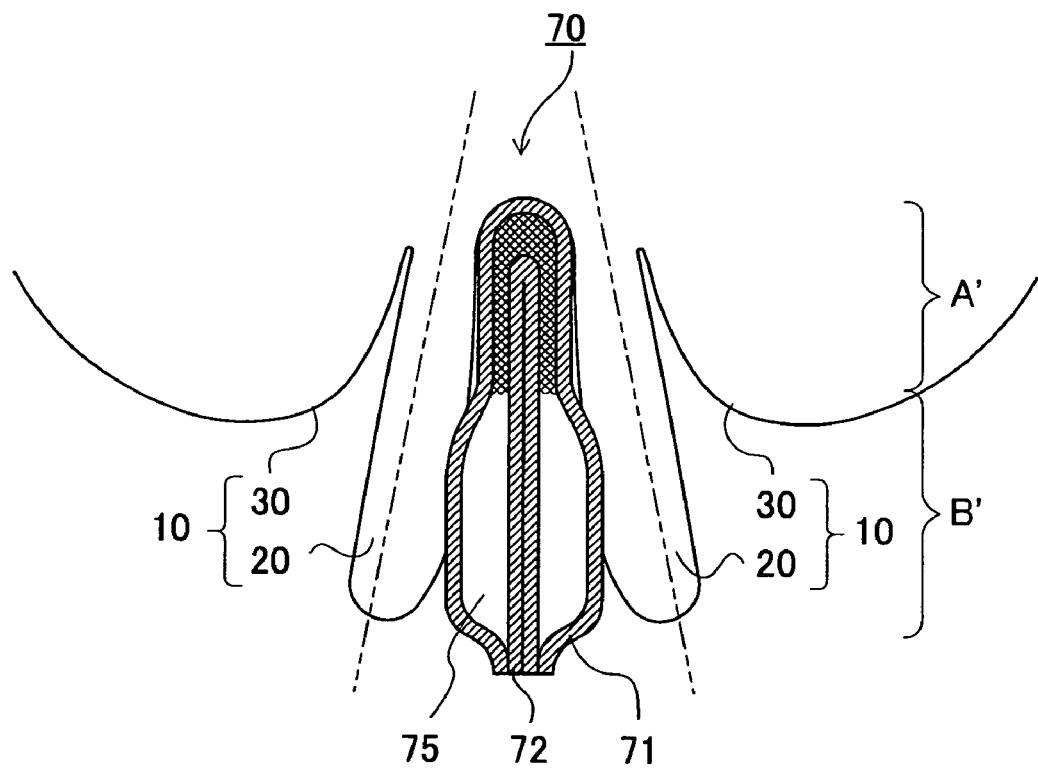
FIG. 25 is a diagram showing the used state of the interlabial pad according to the known example 1.
Figure 26:
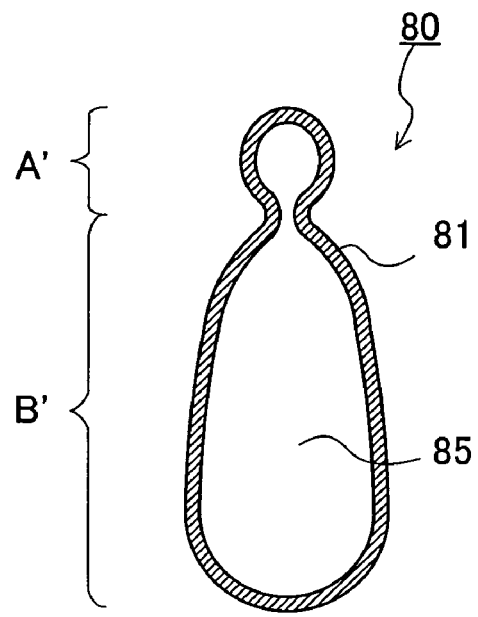
FIG. 26 is a cross-sectional view of the interlabial pad according to the known example 2, taken along a plane perpendicular to the central longitudinal axis of the pad.
Figure 27:
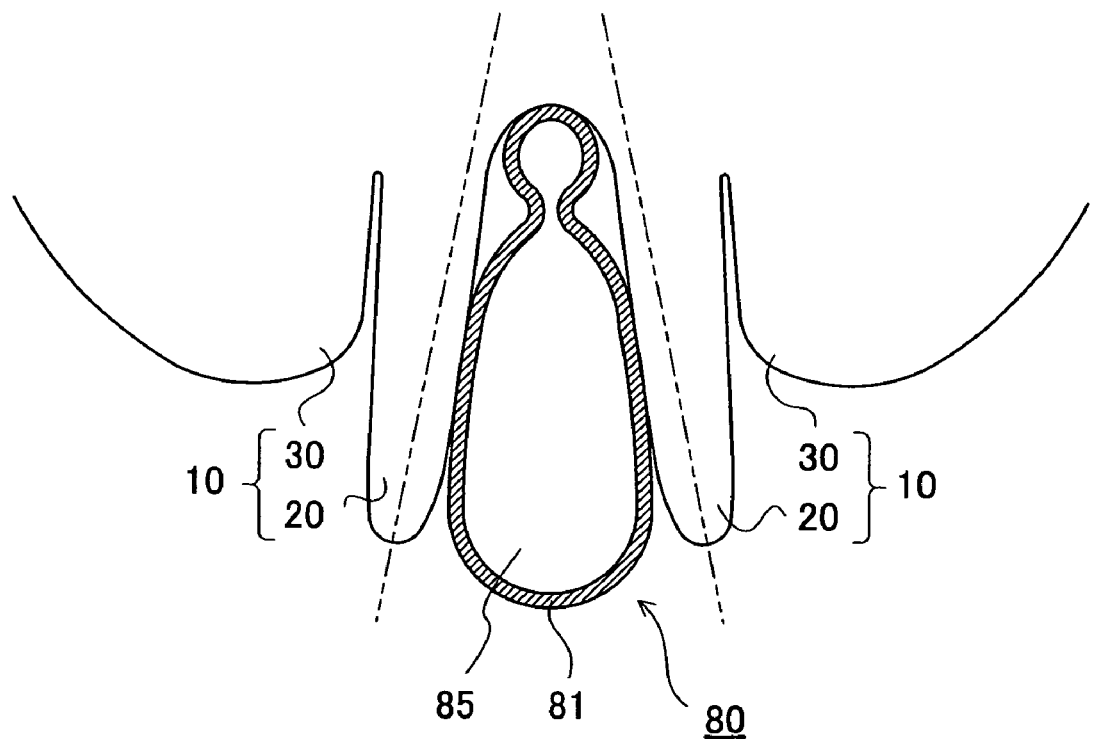
FIG. 27 is a diagram showing the used state of the interlabial pad according to the known example 2.

A known product available from Procter & Gamble Co. Product name "Envive" was used as a comparative sample. As shown in FIG. 24, the comparative sample includes a liquid pervious topsheet, a liquid impervious backsheet and an absorbent body interposed therebetween, and designed for a wearer to fold the pad about the central longitudinal axis of the pad for wearing. A portion contacting near the vestibule floor and a portion contacting near the anterior ends of the labia minora pudenda are substantially equal in thickness and density to each other.

[Estimation]

Compression repulsive forces from the first portion "A" and the second portion "B" were measured for each of the examples 1 through 3 and the comparative sample 1. Estimation derived from the measurement is shown in Table 1. In this case, the compression repulsive force measured for only the absorbent body of each of the interlabial pads was used as measurement values of compression repulsive forces. The reason is due to the fact that although a compression repulsive force varies depending on a covering member enclosing the absorbent body and bonding method for bonding the covering member and the absorbent body, a most significant factor affecting the compression repulsive force is an absorbent body which can account for a significant portion of total weight of the interlabial pad and thus the measurement on the absorbent body yields a fair estimation.

TABLE 1

| No. | | | | Comparative sample 1 | Example1 | Example2 | Example3 Upper layer | Example3 Lower layer |
|---|---|---|---|---|---|---|---|---|
| Absorbent body in the first portion | | Manufacturing method | | Opening/collecting fibers | Opening/collecting fibers | Opening/collecting fibers | Opening/collecting fibers | Opening/collecting fibers |
| | | Material | | Cellulose based fiber assembly | Pulp: 100% Fiber length 1~8 mm | Pulp:100% Fiber length 1~8 mm | Rayon: 85% Stiffness: 3.3 dtx Fiber length 51 mm Natural cotton: 15% | Pulp: 100% Fiber length 1~8 mm |
| | | Specific weight per unit | | 360 | 700 | 700 | 180 | 400 |
| | | Treatment | | Embossed area ratio for dot pattern: 0.5% | Embossed area ratio for dot pattern: 0.5% | Embossed area ratio for dot pattern: 10% | Embossed area ratio for dot pattern: 0.1% | Embossed area ratio for dot pattern: 0.1% |
| Absorbent body in the second portion | | Manufacturing method | | Opening/collecting fibers | Opening/collecting fibers | Opening/collecting fibers | Opening/collecting fibers | — |
| | | Material | | Cellulose based fiber assembly | Pulp: 100% Fiber length 1~8 mm | Pulp: 100% Fiber length 1~8 mm | Rayon: 85% Stiffness: 3.3 dtx Fiber length 51 mm Natural cotton: 15% | — |
| | | Specific weight per unit | | 360 | 300 | 700 | 180 | — |
| | | Treatment | | Embossed area ratio for dot pattern: 0.5% | Embossed area ratio for dot pattern: 0.5% | Embossed area ratio for dot pattern: 0.5% | Embossed area ratio for dot pattern: 0.5% | — |
| Shape of pad held between labia | | | | Twofold | Rectangular parallelepiped | Rectangular parallelepiped | Twofold | |
| Absorbent body in the first portion | Thickness & fiber density | To(0.5/cm$^2$) | mm | 11.5 | 11.2 | 11.2 | 12.8 | |
| | | Fiber density | g/m$^3$ | 0.063 | 0.063 | 0.063 | 0.091 | |
| | | To × 0.7 thickness after 30% reduction of thickness | mm | 8.1 | 8.5 | 8.5 | 9.0 | |
| | | ①Compression repulsive force To × 0.7(mm) | g/m$^2$ | 32 | 36 | 36 | 63 | |
| Absorbent body in the second portion | Thickness & fiber density | To(0.5/cm$^2$) | mm | 11.5 | 11.2 | Apparent 11.2 (Actual 8.8) | 11.0 | |
| | | Fiber density | g/cm$^3$ | 0.063 | 0.027 | Apparent 0.063 (Actual 0.184) | 0.033 | |
| | | To × 0.7 thickness after 30% reduction of thickness by compression | mm | 8.1 | 8.5 | 8.5 | 7.7 | |
| | | ②Compression repulsive force 1 To × 0.3(mm) | g/m$^2$ | 32 | 17 | 3 | 10 | |
| ①/② | | ratio | ratio | 1.0 | 2.1 | 12.0 | 6.3 | |

In the example 1, the compression repulsive force from the first portion "A" was 2.1 times the compression repulsive force from the second portion "B". Accordingly, even when the pad was compressed by a high interlabial pressure applied to the first portion "A", the first portion "A" was hardly going to crumple and the anterior ends of the labia minora pudenda remained parallel to each other or pointed inside a wearer's body. Therefore, the likelihood of falling-off of the pad and leakage of bodily exudates was substantially eliminated.

In the example 2, the compression repulsive force from the first portion "A" was 12 times the compression repulsive force from the second portion "B". Further, the compression repulsive force from the second portion "B" was relatively low, i.e., 3 g/cm$^2$. This means that the anterior ends of the labia minora pudenda were pointing inside the wearer's body and therefore the likelihood of falling-off of the pad and leakage of bodily exudates was substantially eliminated.

In the example 3, the compression repulsive force from the first portion "A" was 6.3 times the compression repulsive force from the second portion "B". This means that the anterior ends of the labia minora pudenda were pointing inside the wearer's body and the surface of the interlabial pad was able to tightly contact the inner wall of the labia without any gap in between, and therefore the likelihood of falling-off of the pad and leakage of bodily exudates was substantially eliminated.

In the comparative sample 1, the compression repulsive forces from the portion contacting near the vestibule floor and the portion contacting near the anterior ends of the labia minora pudenda were substantially equal to each other. This means that the anterior ends of the labia minora pudenda were pointing outside the wearer's body and therefore the likelihood of falling-off of the pad and leakage of bodily exudates was substantially high.

What is claimed is:

1. An interlabial pad having a substantially vertically elongated shape and comprising a top sheet, a back surface sheet and an absorbent body disposed between the top sheet and the back surface sheet,
the interlabial pad being folded in two along a central longitudinal axis such that the back surface sheet faces itself and configured such that a wearer can wear the pad so that a portion of the pad near the central longitudinal axis of the pad is aligned in use with the vestibular floor of the wearer and at least a part of the pad resides within a labia minora pudenda between labia of the wearer, wherein:
the interlabial pad includes a first portion configured to make contact with the wearer in use near the vestibular floor and a second portion configured to make contact with the wearer in use near anterior ends of the labia minora pudenda,
the interlabial pad is folded such that at least a portion of the back surface sheet corresponding to the second portion makes contact with the wearer during use,
the absorbent body is formed as a single layer, and
the absorbent body as positioned at the first portion is thicker than another part of the absorbent body in the second portion in a state in which the interlabial pad is folded in two and also in a state in which the interlabial pad is not folded in two such that a compressive repulsive force generated by compressing the first portion is greater than a compressive repulsive force generated by compressing the second portion.

2. The interlabial pad according to claim 1, wherein a ratio of the compressive repulsive force from the first portion with respect to the compressive repulsive force from the second portion is 1.2 to 10.

3. The interlabial pad according to claim 1, wherein a ratio of the fiber density of the part of the absorbent body in the first portion with respect to the fiber density of another part of the absorbent body in the second portion is 1.2 to 10.

4. The interlabial pad according to claim 1, wherein a ratio of a thickness of a part of the absorbent body in the first portion with respect to a thickness of another part of the absorbent body in the second portion is 1.2 to 10.

5. The interlabial pad according to claim 1, wherein the part of the absorbent body in the first portion has fibers disposed thereon and oriented by crossing over the vicinity of the central longitudinal axis of the pad.

6. The interlabial pad according to claim 1, wherein the first portion has an elastic sheet provided therein.

7. The interlabial pad according to claim 1, wherein the portion has provided therein an expandable member capable of absorbing water and then increasing a volume of the member.

8. The interlabial pad according to claim 1, wherein the lengths of the first and second portions are each about 7 mm.

9. The interlabial pad according to claim 1, wherein:
the interlabial pad is configured so that, when unfolded, the first portion extends about 7 mm from each side of the central longitudinal axis toward edges of the first portion, and two second portions extend about 7 mm outwardly away from each of the edges of the first portion.

10. The interlabial pad according to claim 9, wherein:
the first portion further comprise a front side located frontwardly with respect to the central longitudinal axis and a rear side located rearwardly with respect to the central longitudinal axis, and
the first portion is further configured such that a compressive repulsive force generated by compressing the front side of the first portion is greater than a compressive repulsive force generated by compressing the rear side of the first portion.

11. The interlabial pad according to claim 1, wherein the interlabial pad is made from at least one of a flushable material that collapses upon wet loading and a biodegradable material.

12. The interlabial pad according to claim 1, wherein the first portion is provided with at least one slit in a direction crossing the central longitudinal axis, the slit dividing the first portion so as to impede transmission of an external pressure applied to the first portion, and the at least one slit includes perforation slits.

13. The interlabial pad according to claim 12, wherein the perforation slits have a slit length between 5 mm and 20 mm.

14. The interlabial pad according to claim 12, wherein the perforation slits have a slit pitch between 5 mm and 20 mm.

15. The interlabial pad according to claim 12, wherein the at least one slit is provided in a zigzag pattern.

16. The interlabial pad according to claim 1, wherein
the first portion extends from an end at a surface side in the central longitudinal axis of the interlabial pad toward another end at a side of outer peripheral edge of the interlabial pad, and
the second portion extends from the another end of the first portion to the outer peripheral edge of the interlabial pad.

* * * * *